United States Patent [19]
Saito et al.

[11] Patent Number: 6,157,696
[45] Date of Patent: *Dec. 5, 2000

[54] X-RAY CT SCANNER WITH TWO-DIMENSIONAL X-RAY DETECTOR HAVING UNEQUAL ELEMENT PITCH IN SLICE-THICKNESS DIRECTION

[75] Inventors: Yasuo Saito, Nishinasuno-Machi; Kazuyuki Ihira, Shiobara-Machi; Katsuyuki Taguchi, Nishinasuno-Machi; Tatsuro Suzuki, Utsunomiya; Hiroaki Miyazaki, Otawara; Koichi Muraki, Nishinasuno-Machi; Hiroshi Aradate, Otawara, all of Japan

[73] Assignee: Kabushiki Kaisha Toshiba, Kawasaki, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/891,709

[22] Filed: Jul. 9, 1997

[30] Foreign Application Priority Data

Jul. 12, 1996 [JP] Japan .................................. 8-183866

[51] Int. Cl.⁷ .................................................. H05G 1/60
[52] U.S. Cl. ...................................... 378/19; 250/370.09
[58] Field of Search .......................... 378/19; 250/370.09

[56] References Cited

U.S. PATENT DOCUMENTS

| | | | |
|---|---|---|---|
| 4,725,734 | 2/1988 | Nishiki | ...................................... 379/19 |
| 4,747,117 | 5/1988 | Albrecht et al. | ......................... 378/19 |
| 4,965,726 | 10/1990 | Heuscher et al. | . |
| 5,430,784 | 7/1995 | Ribner et al. | . |

FOREIGN PATENT DOCUMENTS 63-62215   12/1988   Japan .
6-169912    6/1994   Japan .

*Primary Examiner*—Craig E. Church
*Attorney, Agent, or Firm*—Oblon, Spivak, McClelland, Maier & Neustadt, P.C.

[57] ABSTRACT

A multi-slice X-ray CT scanner is provided to realize high resolution and a wide scanned region in a slice-thickness direction for an object. In the X-ray CT scanner, an X-ray beam for slice imaging is radiated toward an object and scanned in a predetermined slice-thickness direction, a direction orthogonal to the slice-thickness direction being defined as a channel direction. The scanner comprises a two-dimensional X-ray detector, a data acquisition system, and an electrically combining unit. The detector has a plurality of X-ray detecting elements arranged in a two-dimensional array of both rows in the slice-thickness direction and columns in the channel direction, the detecting elements of each row being arranged in unequal pitches. The data acquisition system has a plurality of data acquiring elements arranged in a two-dimensional array of rows and columns, acquiring signals detected by the two-dimensional X-ray detector, and producing digital data proportional to the detected signals. The electrically combining unit electrically combines more than two columns of all the columns in the array of the X-ray detecting elements into at least two columns of all the columns in the array of the data acquiring elements in accordance with a given slice imaging condition. For example, each row of the array of the data acquiring elements are less in number of elements than each row of the array of the X-ray detecting elements.

17 Claims, 24 Drawing Sheets

RESOLUTION-CONSCIOUS STRUCTURE
(30 SEGMENTS OF 1mm WIDE ARE ARRANGED)
(a) SEGMENT STRUCTURE
(b) HIGH-RESOLUTION MODE: 1mm×10-slice
(c) MAXIMUM SCANNED REGION MODE: 3mm×10-slice
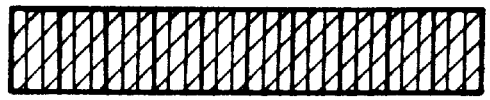
PRIOR ART  FIG. 28A
SCANNED REGION-CONSCIOUS STRUCTURE
(30 SEGMENTS OF 2mm WIDE ARE ARRANGED)
(a) SEGMENT STRUCTURE
(b) HIGH RESOLUTION MODE: 2mm×10-slice
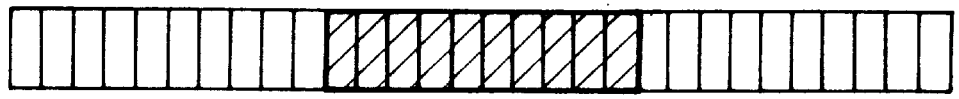
(c) MAXIMUM SCANNED REGION MODE: 6mm×10-slice
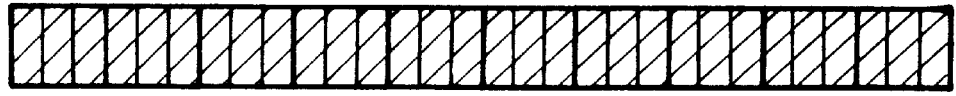
PRIOR ART  FIG. 28B

X-RAY CT SCANNER WITH TWO-DIMENSIONAL X-RAY DETECTOR HAVING UNEQUAL ELEMENT PITCH IN SLICE-THICKNESS DIRECTION

BACKGROUND OF THE INVENTION

1. Field of the Invention

The present invention relates to an X-ray CT scanner including a two-dimensional detector that has a plurality of columns (a plurality of segments) thereof laid out in the direction of the axis of rotation of a gantry (in the direction of a center axis about which an X-ray focal spot is rotated, or simply, the direction of the thickness of a slice plane (slice thickness)), and that has the widths of the plurality of columns thereof defining slice thicknesses (slice pitches) made unequal.

2. Description of the Related Art

X-ray CT scanners include a fan-beam (single-slice) X-ray CT scanner or a type of X-ray CT scanner that has been adopted in the past.

The fan-beam X-ray CT scanner has an X-ray source and detector opposed to each other with a subject (for example, a patient) between them. The detector has detecting elements, which constitute, for example, approximately 1000 channels, arranged in the form of a sector in a (channel) direction orthogonal to a body-axial direction of the subject.

In the X-ray CT scanner, a fan-shaped X-ray beam is irradiated from the X-ray source to a certain slice plane (or, simply, a slice) of the subject. An X-ray beam transmitted by the slice plane of the subject is detected by the detector, and then X-ray transmission data is acquired.

The acquired X-ray transmission data is sent to a data acquisition system (DAS) having elements associated with the detecting elements of the detector. Each element carries out amplification or the like and acquires projection data (one data acquisition is referred to as one view).

While the X-ray source and detector are rotated in unison about the subject, X-rays are irradiated and data acquisition is repeated approximately 1000 times. Consequently, projection data in multiple directions of the subject is acquired. Based on the projection data in multiple directions, the image of the slice plane of the subject is reconstructed.

In such a single-slice X-ray CT scanner, the image of a certain slice plane of a subject is produced. It is therefore hard to produce images of a wide range of the subject for a short period of time. There is therefore an increasing demand from doctors and the like for producing high-definition (high-resolution) images of a wide range of a subject for a unit period of time.

In an effort to meet the demand, studies have been made on a multi-slice X-ray CT scanner in recent years.

The multi-slice X-ray CT scanner has a plurality of columns (a plurality of (N) segments) of detectors, each of which is the same as the one employed in the single-slice X-ray CT scanner, in the body-axis direction of a subject (also referred to as a slice-thickness direction or segment direction). The detectors constitute a two-dimensional detector having detecting elements numbering the product of M channels by N segments. In this case, elements of a DAS are associated with the detecting elements of the two-dimensional detector.

In other words, the multi-slice X-ray CT scanner has an X-ray source for bombarding a conical X-ray beam, and the foregoing two-dimensional detector. X-rays of the conical X-ray beam (diameter of an effective field of view, FOV) passing through a subject are detected by the two-dimensional detector, whereby projection data of multiple slice planes of the subject is acquired at a time. Thus, the multi-slice X-ray CT scanner is expected to enable acquisition of high-definition images from a wide range.

Various proposals have been made of the configurations of such a multi-slice X-ray CT scanner and two-dimensional detector employed in the multi-slice X-ray CT scanner.

For example, known is an idea of freely changing one slice thickness by combining X-ray data items detected by a plurality of segments through image post-processing based on detected data.

Thinking of the specifications of a two-dimensional detector and DAS for a multi-slice X-ray CT scanner, several parameters have significant meanings. To be more specific, for improving the resolution in a body-axis direction, it is necessary to finely set the pitches in the body-axis direction of elements corresponding to segments of the detector (slice thickness) relative to adjoining ones. For expanding a scanned region in the body-axis direction (for eventually shortening the scan time of a certain region), the size of the whole detector (the number of the columns corresponding to the segments of the detector) must be made larger. In an effort to clear both the requirements that are seemingly contradictory, that is, improvement of the resolution in the body-axis direction and expansion of a scanned region, it has been conceived that sufficiently small detecting elements that are fine divisions of a detector are arranged in the body-axis direction by the number of columns (segments) defining a sufficiently large size.

However, on the detector side, there are limitations in a minimum size of an element (in a slice-thickness direction) and a maximum number of elements because of the problems that geometrical efficiency is deteriorated with finer segmentation of the detector and that the density of wiring patterns increases with an increase in number of elements. It is therefore currently thought that approximately 1 mm and approximately 30 columns are feasible levels of the minimum size of an element and of the maximum number of columns of elements respectively.

For arranging approximately 30 columns of detecting elements, it is necessary to install a DAS having the number of elements corresponding to the number of segments or columns of the detecting elements. A simple countermeasure is to arrange a plurality of (30) columns of currently-employed DASs. In reality, there are limitations in the number of elements of a DAS that can be arranged because of the problem of preserving an installation space in a scanner system or the problem of ensuring appropriate cost performance. The existing high-density installation technology and manufacturing cost permit about 10 columns of elements as a level feasible in the near future.

Since restrictions are thus placed differently on the parameters such as the number of elements of a DAS, a minimum size of an element of a detector, and a maximum number of elements in the detector, it is hard to attain high resolution in the body-axis direction and a wide scanned region by nonchalantly combining these parameters. A further commitment to novelties and improvements is requested.

FIGS. 28A and 28B show examples of a combination of parameters according to a prior art, that is, examples of a row of detecting elements of a detector constituting one channel in such a connection mode that a detector composed of 30 columns of detecting elements having an equal pitch (slice thickness) of 1 mm or 2 mm relative to adjoining ones and a DAS having elements that numbers a multiple of 10 slices are combined via a group of switches. FIG. 28A shows a resolution-conscious structure in which the width of a detecting element is set to 1 mm, while FIG. 28B shows a scanned region-conscious structure in which the width of a detecting element is set to 2 mm.

In the resolution-conscious structure, as shown in FIGS. 28Aa, the detector has 30 segments of 1 mm wide arranged. Since the DAS has elements that numbers a multiple of 10 slices, data acquisition can be carried out in the range from data acquisition of a total of 10 slices having a pitch of 1 mm relative to adjoining hones (1 mm×10 slices=10 mm)(See FIGS. 28Ab) to data acquisition of a total of 10 slices having a pitch of 3 mm relative to adjoining ones (3 mm×10 slices=30 mm)(See FIG. 28Ac).

In the resolution-conscious structure, the resolution in a segment direction can be made as fine as 1 mm. However, the scanned region is limited to a maximum of 30 mm or so. A sufficiently wide scanned region is thus unavailable.

By contrast, in the scanned region-conscious structure, as shown in FIGS. 28Ba, the detector has 30 segments of 2 mm wide arranged. Like the resolution-conscious structure, data acquisition can be carried out in the range from realization of a total of 10 slice having a pitch of 2 mm relative to adjoining ones (2 mm×10 slices=20 mm)(See FIG. 28Bb), to realization of a total of 10 slices having a pitch of 6 mm relative to adjoining ones (6 mm×10 slices=60 mm)(See FIG. 28Bc).

In the scanned region-conscious structure, the scanned region is 60 mm at maximum, and thus a sufficiently wide scanned region is provided. However, a minimum slice pitch in the segment direction is as large as 2 mm. Sufficient resolution is unavailable.

For example, when the size of an element in a detector is set to a large value with emphasis placed on a wide scanned region, a desired slice thickness may not be able to be attained. For example, when numerous detecting elements that are segments of 2 mm wide are arranged, slices having, for example, a pitch of 5 mm relative to adjoining ones cannot be specified even by changing the setting of the group of switches designed for combining signals.

As mentioned above, increasing the numbers of detecting elements and of elements of a DAS is preferable for realizing high resolution in the body-axis direction and a wide scanned region. However, there is the fear that an increase in the number of elements may lead to deterioration of reliability of a whole scanner. In consideration of recent technological advancement, it cannot always be said that a failure rate increases in proportion to an increase in the numbers of detecting elements and of elements of a DAS. For limiting the failure rates of a detector having detecting elements numbering a value that is, for example, 30 times as large as the number of detecting elements included in an existing detector and a DAS having elements numbering a value that is, for example, 10 times as large as the number of elements included in an existing DAS to the same failure rates of the existing detector and DAS, reliabilities that are 30 times and 10 times higher than those of the existing detector and DAS are required. Specifically, for increasing the numbers of elements of a detector and elements of a DAS, it is necessary to devise a means for maintaining reliability in case a failure occurs at a rate proportional to the increase.

SUMMARY OF THE INVENTION

The present invention attempts to break through the foregoing circumstances. The first object of the present invention is to provide a multi-slice X-ray CT scanner capable of realizing both high resolution in a slice-thickness direction for an object and a wide scanned region in the slice-thickness direction.

The second object of the present invention is to provide a multi-slice X-ray CT scanner offering the greatly increased freedom in selecting a slice thickness.

The third object of the present invention is to provide an X-ray CT scanner capable of enjoying sufficient reliability even if a failure occurs in a detecting element or an element of a DAS.

For accomplishing the above objects, according to the first aspect of the present invention, there is provided an X-ray CT scanner in which an X-ray beam for slice imaging is radiated toward an object and scanned in a predetermined slice-thickness direction, a direction orthogonal to the slice-thickness direction being defined as a channel direction, the scanner comprising: a two-dimensional X-ray detector having a plurality of X-ray detecting elements arranged in a two-dimensional array of both rows in the slice-thickness direction and columns in the channel direction, the detecting elements of each row being arranged in unequal pitches; a data acquisition system having a plurality of data acquiring elements arranged in a two-dimensional array of rows and columns, acquiring signals detected by the two-dimensional X-ray detector, and producing digital data proportional to the detected signals; and means for electrically combining more than two columns of all the columns in the array of the X-ray detecting elements into at least two columns of all the columns in the array of the data acquiring elements in accordance with a given slice imaging condition.

Preferably, each row of the array of the data acquiring elements are less in number of elements than each row of the array of the X-ray detecting elements. As an example, the two-dimensional array of the X-ray detecting elements are arranged based on an unequal pitch structure wherein a first detecting element having a specified minimum slice pitch is positioned in the center of each row and second detecting element having greater slice pitch than the minimum slice pitch are positioned in outer-sides for the center of each row, both the first detecting element and the second detecting elements making up the X-ray detecting elements. Still as an example, the combining means comprises a group of a plurality of switches for on/off-switching between the X-ray detecting elements residing in each row and the data acquiring elements residing in each row, and means for controlling an on/off state of each of the switches in reply to the given slice imaging condition.

It is also preferred that the controlling means includes an element controlling the on/off state of each of the switches so that data outputted from the data acquiring elements residing in each row form a tomographic slice image having one specified slice thickness.

Also preferred is a construction that the controlling means includes an elements controlling the on/off state of each of the switches so that at least three X-ray detecting elements including the first detecting element in each row are connected to at least two data acquiring elements of each row when the given slice imaging condition includes a slice-thickness of a tomographic slice image of the object, the slice-thickness being greater than the specified minimum slice pitch. In this case, preferably, the unequal pitch of each row of the X-ray detecting elements is set such that the slice thickness of the tomographic slice image broadens every two times of thickness for each combination of the X-ray detecting elements in each row, each combination being instructed by the controlling means responding to changes in the slice-thickness included in the slice imaging condition.

It is preferred that the unequal pitch of each row of the X-ray detecting elements is set such that the slice thickness of the tomographic slice image broadens every three times of thickness for each combination of the X-ray detecting elements in each row, each combination being instructed by the controlling means respondingly to changes in the slice-thickness included in the slice imaging condition.

It is still preferred that the switches of the switch group are arranged so as to connect each of the X-ray detecting elements of each row to each of the data acquiring elements of each row corresponding to each row of the X-ray detecting elements.

Also preferable is that the switches so as to only connect desired ones of the X-ray detecting elements of each row, which are required to realize a desired on/off switch control pattern for the controlling means, to the data acquiring elements of each row corresponding to each row of the X-ray detecting elements.

As an example, the scanner can be further comprises a beam trimmer having two X-ray shielding plates movable along the slice-thickness direction and arranged on an X-ray incidence surface side of the two-dimensional X-ray detector, and further means for controlling an edge position of each of the X-ray shielding plates in the slice-thickness direction in accordance with a slice thickness included in the slice imaging condition, thereby both the on/off control of each of the switches by the control means and the edge position control of each of the X-ray shielding plates permitting data acquisition of desired slice pitches at output of the data acquisition system.

As another example, the scanner of the above basic components further comprises means for detecting a failing element residing in either one of the X-ray detecting elements and the data acquiring elements, and means for correcting detected data from the failing element on the basis of a two-dimensional position of the failing element detected by the detecting means. In this case, as an example, the failing element is that of the X-ray detecting elements, and detected data correcting means comprises first means for determining if there is a accomplished first state that the failing element detects data occupying all or almost all of the data acquired by the data acquiring elements, second means for determining if there is accomplished a second state that the data detected by the failing element is positioned in the slice-thickness direction in edges of a group of data acquired by the entire data acquiring elements when the first state has been accomplished, first means for interpolating the data from the failing element with detected data from three elements surrounding the failing element when the second state has been accomplished, second means for interpolating the data from the failing element with detected data from four elements surrounding the failing element when an opposite state to the second state has been accomplished, and means for correcting sensitivity data of corresponding data from the entire x-ray detecting elements when an opposite state to the first state has been accomplished.

As another aspect, there is provided an X-ray CT scanner in which an X-ray beam for slice imaging is radiated toward an object and scanned in a predetermined slice-thickness direction, a direction orthogonal to the slice-thickness direction being defined as a channel direction, the scanner comprising: a two-dimensional X-ray detector having a plurality of X-ray detecting elements separated by separators and arranged in a two-dimensional array of both rows in the slice-thickness direction and columns in the channel direction, the detecting elements of each row being arranged in unequal pitches; and a data acquisition system having a plurality of data acquiring elements arranged into a two-dimensional array of rows and columns, acquiring signals detected by the two-dimensional X-ray detector and producing digital data proportional to the detected signals, wherein the separators includes a sub separator placed along the slice-thickness direction and made of a thin film of metal.

It is preferred that the scanner further comprises means for electrically combining more than two columns of all the columns in the array of the X-ray detecting elements into at least two columns of all the columns in the array of the data acquiring elements in accordance with a given slice imaging condition.

According to the present invention, the detecting elements belonging to each of a plurality of rows of detecting elements, laid out in a slice-thickness direction, constituting channels are structured so that the pitches of the detecting elements relative to adjoining elements are unequal (for example, a reference segment whose pitch relative to an adjoining segment corresponds to a minimum slice pitch is located in the center in the slice-thickness direction, and segments whose pitches relative to adjoining segments correspond to larger slice pitches than the minimum slice pitch are arranged on both sides of the reference segment in the slice-thickness direction). The detecting elements of each row of detecting elements having the unequal pitches, and some of the plurality of data acquisition elements laid out in the slice-thickness direction and channel direction, which are associated with the detecting elements of each row of detecting elements (the number of data acquisition elements is smaller than the number of X-ray detecting elements in a slice-thickness direction) are selectively connected by controlling the on or off states of a group of switches composed of a plurality of switches which serves as a detecting element selecting means according to the condition of a slice thickness.

For obtaining slice data of slices having a fine slice thickness (for example, data of slices having a minimum slice thickness) using the data acquisition elements, the reference segment is selected and then segments are connected to the data acquisition elements. For expanding a scanned region, if the segments constituting each row of detecting elements are connected to the data acquisition elements in an ordinary manner, since the number of segments constituting each row of detecting elements is larger than the number of data acquisition elements as mentioned above, only a scanned region defined by the number of data acquisition elements can be realized.

In the present invention, at least part of a plurality of segments including a reference segment and constituting each row of detecting elements are combined and connected to a given data acquisition element among data acquisition elements associated with each row of detecting elements. Thus, for example, all the segments can be connected to the data acquisition elements. As a result, high resolution (fine slice pitch) in a slice-thickness direction and a wide scanned region therein can be realized.

According to the present invention, when the way of combining a plurality of segments, which have unequal pitches relative to adjoining segments and constitute each row of detecting elements of a two-dimensional detector, is changed according to a change in the condition of a slice thickness, the thicknesses of slices whose data is acquired by the data acquisition elements are doubled. Data of slices having the thicknesses dependent on an object of diagnosis can be acquired.

Furthermore, while the on or off states of the switches are controlled by a switch control means, the positions of the edges of a fan beam defined by a beam trimmer are controlled. Consequently, data of slices having such a thickness that could have hardly been realized in the past can be acquired.

Furthermore, according to the present invention, if a certain X-ray detecting element of a two-dimensional detector fails, an optimal one of various correction processes (interpolation using data items detected by adjoining elements, correction of the sensitivity of the detector by considering that data except a data item provided by the failing element is detected, and the like) is chosen on the basis of the position of the failing element (for example, whether or not data detected by the failing element is located at an end in a slice direction of a group of acquisition data items to be acquired by all the data acquisition elements). According to the optimal process, data detected by the failing element is corrected. Therefore, if a detecting element should fail, an optimal measure can be taken all the time.

BRIEF DESCRIPTION OF THE DRAWINGS

In the accompanying drawings:

FIG. 6A shows data acquisition of 8 slices of 1 mm thick, and FIG. 6B shows data acquisition of 8 slices of 2 mm thick;

FIG. 7A shows data acquisition of 8 slices of 4 mm thick, and FIG. 7B shows data acquisition of 8 slices of 8 mm thick;

FIG. 8A shows data acquisition of a slice of 26 mm thick, six slices of 2 mm thick, and a slice of 26 mm thick, and FIG. 8B shows data acquisition of a slice of 12 mm thick, six slices of 4 mm thick, and a slice of 12 mm thick;

FIG. 9A shows data acquisition of a slice of 10 mm thick, six slices of 2 mm thick, and a slice of 10 mm thick, FIG. 9B shows data acquisition of a slice of 10 mm thick, a slice of 3 mm thick, a slice of 2 mm thick, a slice of 1 mm thick, a slice of 1 mm thick, a slice of 2 mm thick, a slice of 3 mm thick, and a slice of 10 mm thick;

FIG. 11A shows data acquisition of 4 slices of 1 mm thick, and FIG. 11B shows data acquisition of 4 slices of 2 mm thick;

FIG. 12A shows data acquisition of 4 slices of 4 mm thick, and FIG. 12B shows data acquisition of 4 slices of 8 mm thick;

FIG. 13A shows data acquisition of 6 slices of 1 mm thick, and FIG. 13B shows data acquisition of 6 slices of 2 mm thick;

FIG. 14A shows data acquisition of 6 slices of 4 mm thick, and FIG. 14B shows data acquisition of 6 slices of 8 mm thick;

FIG. 16A shows data acquisition of 3 slices of 1 mm thick, FIG. 16B shows data acquisition of 3 slices of 3 mm thick, and FIG. 16C shows data acquisition of 3 slices of 9 mm thick;

FIG. 18A shows data acquisition of 6 slices of 1 mm thick, and FIG. 18B shows data acquisition of 6 slices of 3 mm thick;

FIG. 20A shows data acquisition of a slice of 2 mm thick, four slices of 1 mm thick, and a slice of 2 mm thick, FIG. 20B shows data acquisition of a slice of 4 mm thick, 4 slices of 2 mm thick, and a slice of 4 mm thick, and FIG. 20C shows data acquisition of a slice of 8 mm thick, four slices of 4 mm thick, and a slice of 8 mm thick;

FIG. 22A is a diagram showing a method using switches alone, and FIG. 22B is a diagram showing a method using a beam trimmer in combination;

FIGS. 28A and 28B are diagrams showing structures of segments having an equal pitch relative to adjoining segments according to a prior art, FIG. 28A is a diagram showing a resolution-conscious segment structure, and FIG. 28B is a diagram showing a scanned region-conscious segment structure.

DESCRIPTION OF THE PREFERRED EMBODIMENTS

Referring to the appended drawings, an embodiment of the present invention will be described below.

Figure 1:
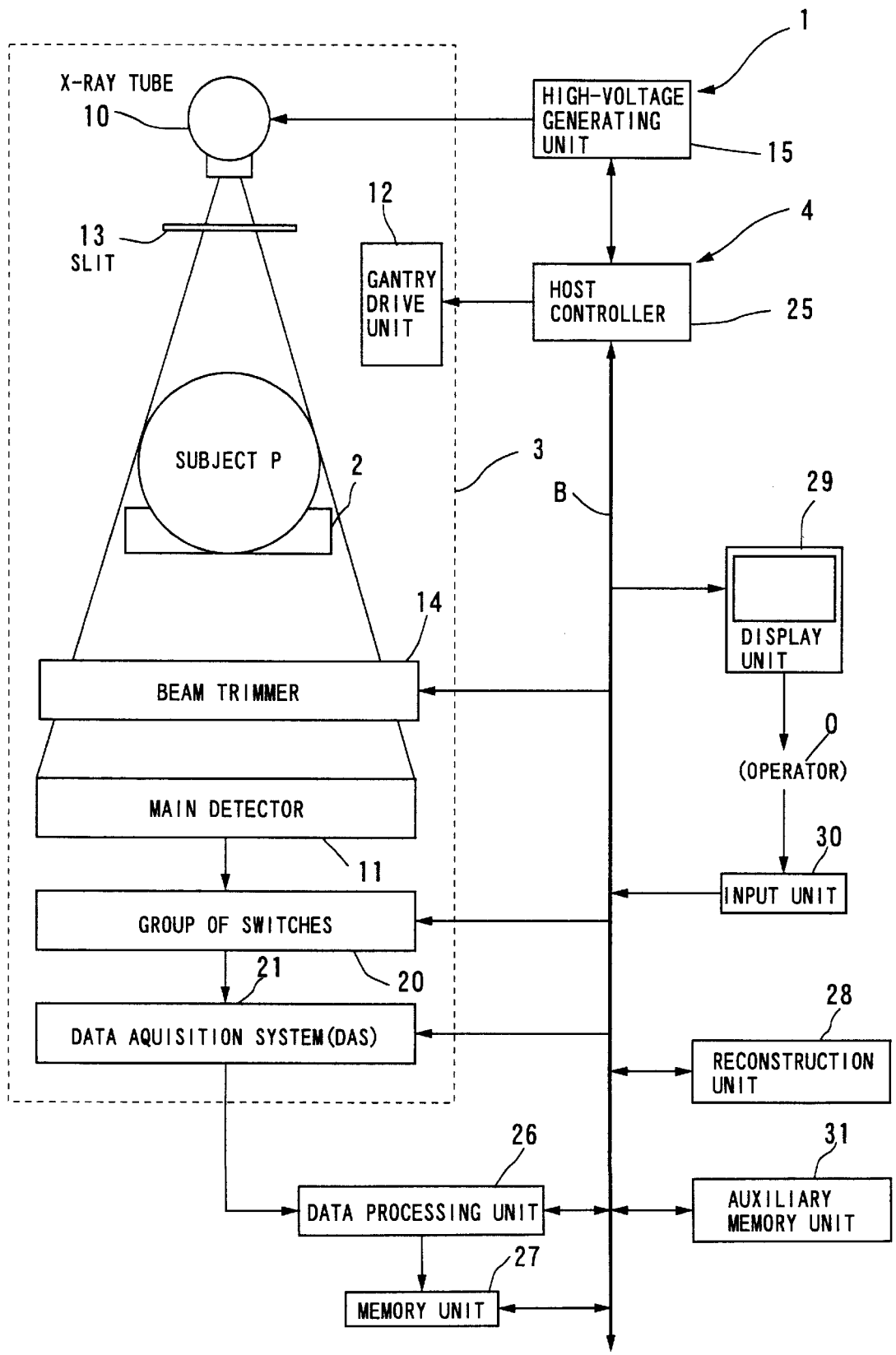
FIG. 1 is a block diagram schematically showing the configuration of an X-ray CT scanner in accordance with an embodiment of the present invention.

FIG. 1 is a block diagram showing the schematic configuration of an X-ray CT scanner 1 of an embodiment.

Referring to FIG. 1, the X-ray CT scanner (CT system) 1 comprises a patient couch 2 on which a subject (patient) P lies down, a gantry 3 having a diagnostic bore, which is not shown, into which the subject P is inserted for diagnosis and acquiring projection data of the subject P, and a system unit 4 for controlling the whole scanner, reconstructing an image on the basis of the acquired projection data, and displaying a reconstructed image.

The patient couch 2 can slide in body-axis directions of the subject P when driven by a couch drive unit that is not shown.

The gantry 3 has an X-ray tube 10 and main detector 11 opposed with the subject P inserted in the diagnostic bore between them, and further includes a gantry drive unit 12. The X-ray tube 10 and main detector 11 can be rotated in unison about a center axis parallel to a body-axis direction of the subject P inserted into the diagnostic bore of the gantry 3 when driven by the gantry drive unit 12. Interposed between the X-ray tube 10 and subject P in the gantry 3 is a slit 13 for reshaping a conical X-ray beam bombarded from the X-ray focal spot in the X-ray tube 10, and thus produce an X-ray beam of a desired size. Located on the incident side of an X-ray beam of the main detector 11 is a beam trimmer 14 having two X-ray shielding plates that move in, for example, column directions of the main detector 11. The beam trimmer 14 trims an X-ray beam passing through the subject P by controlling the positions in the row directions of the main detector 11 to which the two shielding plates are moved according to a condition for scanning (the condition of a slice thickness), and thus produces a transmitted X-ray beam exhibiting a good transmission profile.

Furthermore, the X-ray CT scanner 1 includes a high-voltage generating unit 15 for applying a high voltage to the X-ray tube 10. Application of a high voltage to the X-ray tube 10 by means of the high-voltage generating unit 15 is achieved by, for example, a contact type slip ring mechanism.

Figure 2:
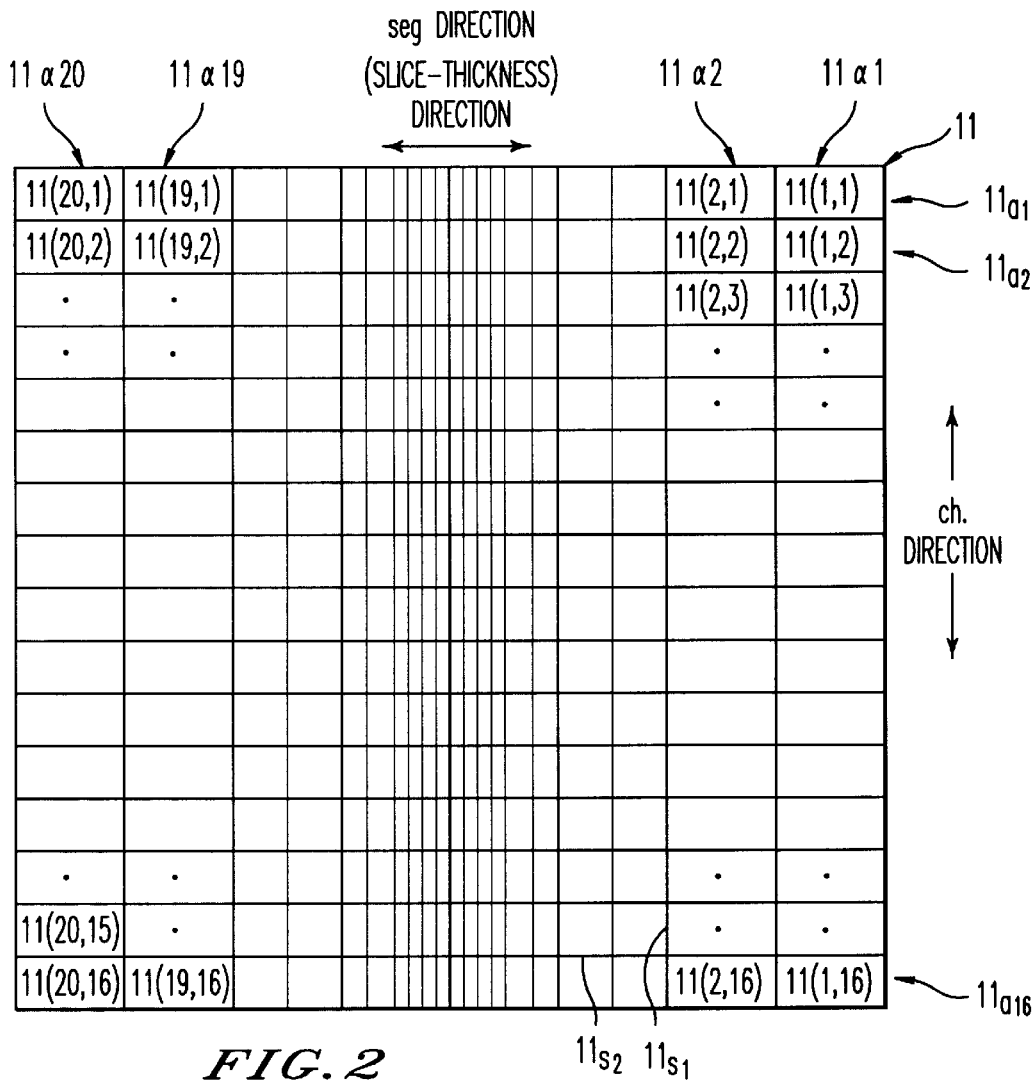
FIG. 2 shows the structure of a main detector (two-dimensional detector)

The main detector 11 is, as shown in FIG. 2, realized as a two-dimensional detector in which a plurality of rows of detecting elements, each of which has a plurality of segments (20 segments in this embodiment) arranged in a segment direction (body-axis direction or slice-thickness direction) and constitute one channel, are laid out in the form of an array in a channel direction in order to constitute a plurality of channels (16 channels in this embodiment) (FIG. 2 shows a two-dimensional detector having an array of 16 channels by 20 segments).

In other words, in FIG. 2, assuming that a row of elements constituting the first channel, which covers 20 segments, is a row of elements $11a1$, rows of elements $11a1$ to $11a16$ constituting the first to sixteenth channels are arranged. Assuming that a column of elements constituting 16 channels which covers the first segment is a column of elements $11\alpha1$, columns of elements $11\alpha1$ to $11\alpha20$ covering the first to twentieth segments are arranged.

Herein, assuming that the position (address) of each of the detecting elements laid out two-dimensionally is expressed in the format of (segment, channel), an element belonging to the first segment and first channel is expressed as an element $11(1,1)$. The elements belonging to the row of elements $11a1$ constituting the first channel are expressed as elements $11(2,1)$, etc., and $11(20,1)$. Likewise, the elements belonging to the remaining rows of elements $11a2$ to $11a16$ are expressed as follows: the elements belonging to the row of elements $11a2$ constituting the second channel are expressed as elements $11(1,2)$, etc., and $11(20,2)$; the elements belonging to the row of elements $11a3$ constituting the third channel are expressed as elements $11(1,3)$ etc. and $11(20,3)$; the elements belonging to the row of elements $11a15$ constituting the fifteenth channel are expressed as elements $11(1,15)$, etc., and $11(20,15)$; and the elements belonging to the row of elements $11a16$ constituting the sixteenth channel are expressed as elements $11(1,16)$, etc., and $11(20,16)$.

Separators (reflector plates) $11s1$ and $11s2$ made of, for example, a metal are interposed between segments and channels respectively, whereby crosstalk between adjoining channels and segments is eliminated.

Slice thicknesses (slice pitches) realized with the widths in a segment direction of the elements of each of the rows of elements $11a1$ to $11a16$ constituting the channels of the main detector (two-dimensional detector) 11 of this embodiment are made unequal so that the slice thicknesses get larger from the center element toward the elements on both ends. The slice pitches that are unequal in the segment direction shall be referred to as unequal pitches.

Figure 3:
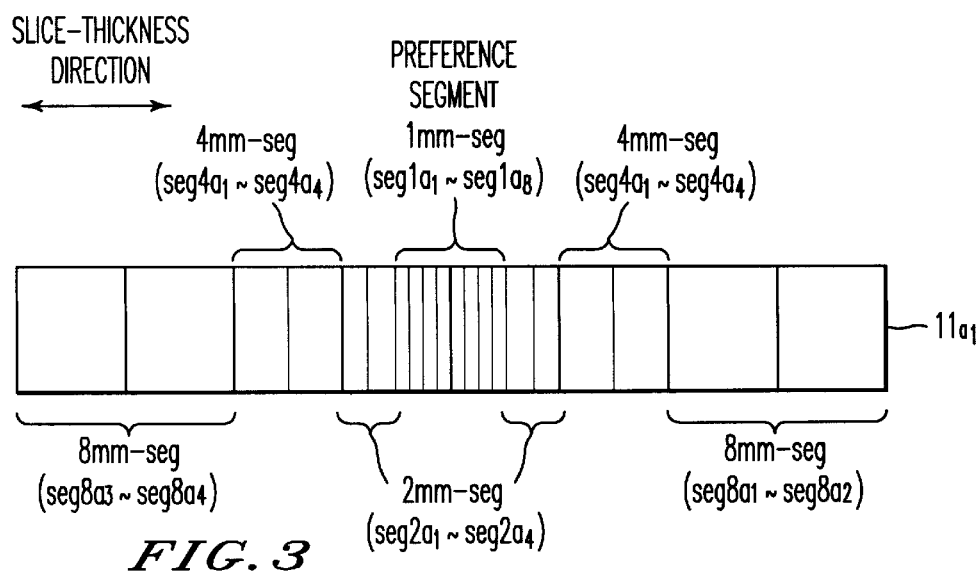
FIG. 3 shows the structure of columns of a detector in such a connection mode that a minimum slice thickness to be realized is 1 mm and the total number of segments is 20.

FIG. 3 is concerned with the structure of each of the rows of elements 11a1 to 11a16 constituting the channels of the main detector 11. FIG. 3 shows the structure of the row of elements 11a1 constituting the first channel.

In this embodiment, a column of detecting elements having a width realizing a minimum slice thickness permitted by the X-ray CT scanner 1 is referred to as a reference segment. In this embodiment, the minimum slice thickness shall be 1 mm.

Referring to FIG. 3, the structure of each of the rows of elements 11a1 to 11a16 constituting the channels of the main detector 11 is such that eight reference segments (segments whose widths correspond to a slice thickness of 1 mm) are laid out in the center (seg1a1 to seg1a8 from the right in the drawing), a total of four segments of 2 mm wide (segments whose widths correspond to a slice thickness of 2 mm) are laid out in twos on both outer sides of the reference segments (seg2a1 to seg2a4 from the right in the drawing), a total of four segments of 4 mm wide (segments whose widths correspond to a slice thickness of 4 mm) are laid out in twos on both outer sides of the segments of 2 mm wide (seg4a1 to seg4a4 from the right in the drawing). Moreover, a total of four segments of 8 mm wide (segments whose widths correspond to a slice thickness of 8 mm) are laid out in twos on both outer sides of the segments of 4 mm wide (seg8a1 to seg8a4 from the right in the drawing). There are thus a total of 20 segments per channel. All the 20 segments come to 64 mm in width. Noted is that these dimensions are values measured in the center of the axis of rotation of the gantry 3 (X-ray tube 10 and main detector 11) but not actual dimensions in the main detector 11.

X-ray transmission data items detected by the detecting elements of the main detector (two-dimensional detector) 11 are sent to a data acquisition system (DAS) 21, which includes data acquisition elements (DAS-1a1 to DAS-8a1, etc. and DAS-1a16 to DAS-8a16) to be associated with 8 columns (8 slices) out of the rows of detecting elements 11a1 to 11a16 constituting the channels (20 segments), via a group of switches 20.

Figure 4:
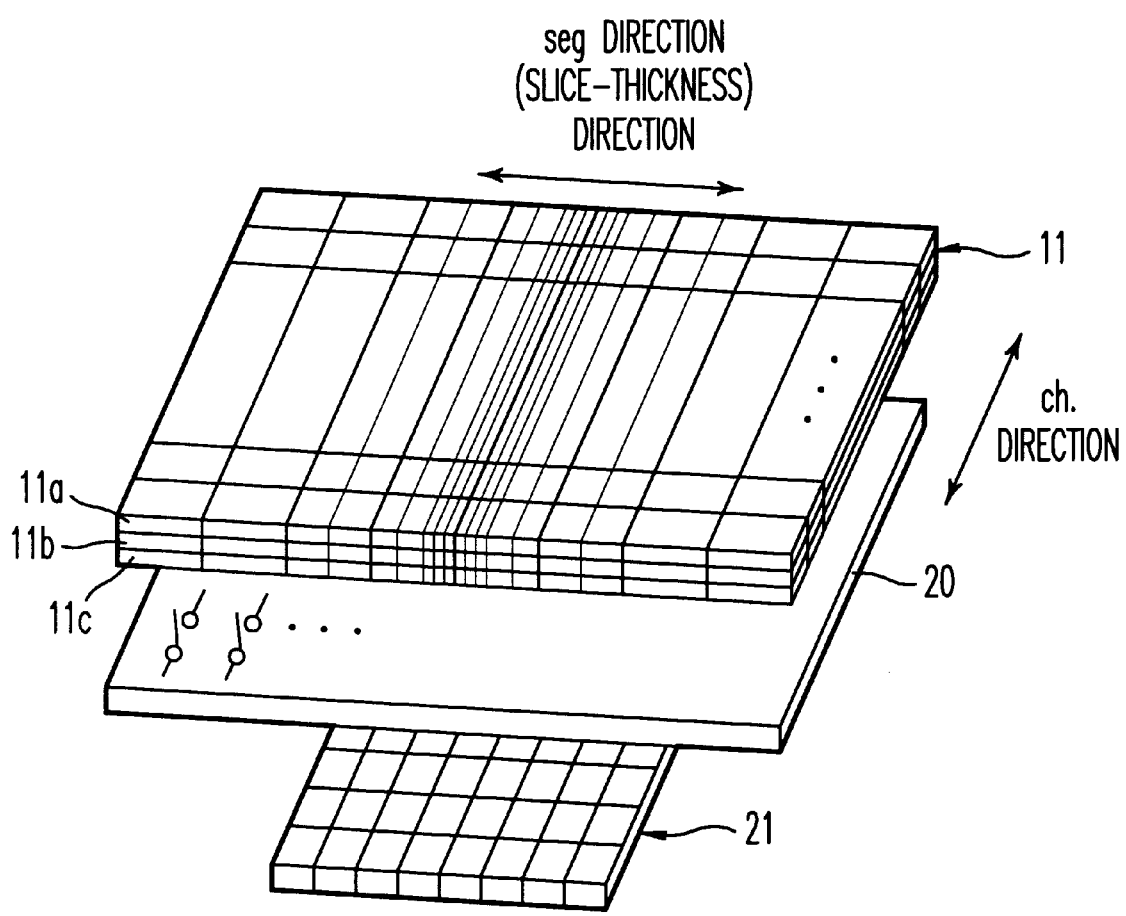
FIG. 4 is an oblique view schematically showing the main detector, a group of switches, and a data acquisition system.

FIG. 4 is an oblique view showing the structures of the two-dimensional detector 11, group of switches 20, and DAS 21 of this embodiment. As shown in FIG. 4, the two-dimensional detector 11 has detecting elements set in array, and the group of switches 20 have switching devices such as FETs mounted on, for example, a switching substrate. Each of the detecting elements is made up of a scintillator layer 11a, a light-transmitting resin layer 11b, and a photodiode layer 11c, thus X-rays reached the scintillator layer being converted to corresponding electric signals via photo signals. Alternatively, a semiconductor detecting device directly converting X-rays to electric signals may be used. The data acquisition elements of the DAS 21 are laid out in the form of an array like the detecting elements of the two-dimensional detector 11.

The data acquisition elements (DAS-1a1 to DAS-8a1, etc., and DAS-1a16 to DAS-8a16) of the DAS 21 acquire projection data of 8 slices of the subject P by amplifying supplied X-ray transmission data items and converting them into digital signals.

Figure 5:
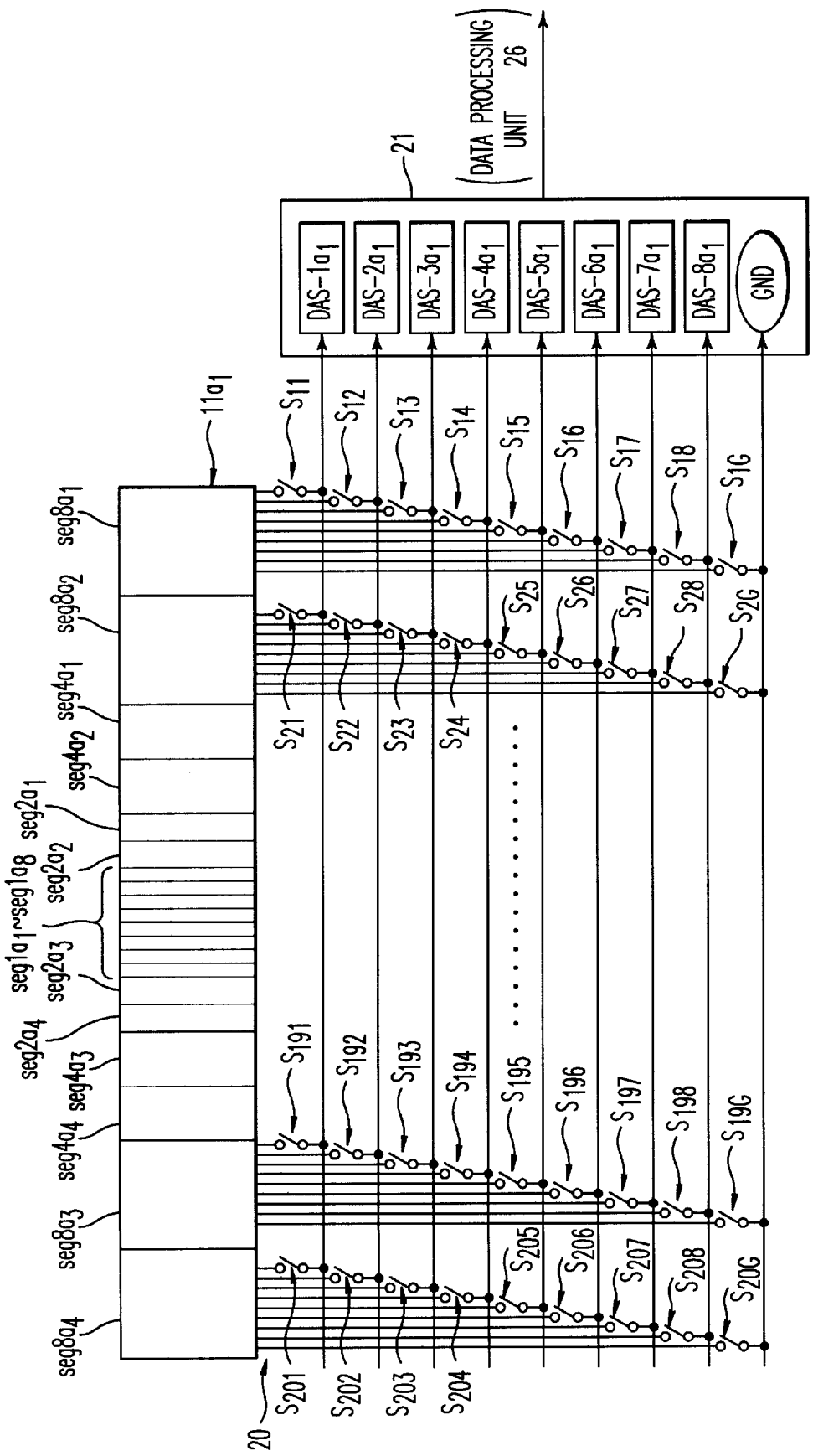
FIG. 5 is a diagram showing an example of the structure of the group of switches in such a connection mode that a DAS designed for handling 8 slices is used to acquire data.

FIG. 5 shows the connectional relationship between the row of detecting elements 11a1 (seg1a1 to seg1a8, seg2a1 to seg2a4, seg4a1 to seg4a4, and seg8a1 to seg8a4) constituting the first channel, which covers 20 segments, within the main detector 11 and the DAS 21 having the data acquisition elements (DAS-1a1 to DAS-8a1) associated with 8 columns (8 slices) out of the row of detecting elements 11a1 constituting the first channel by way of the group of switches 20. For brevity's sake, FIG. 5 shows only a group of switches for connecting the detecting elements seg8a1 to seg8a4 on both ends of the row of detecting element to the data acquisition elements DAS-1a1 to DAS-8a1.

Referring to FIG. 5, the element seg8a1 is connected to the element DAS-1a1 via a switch S11, also connected to the elements DAS-2a1 to DAS-8a1 via switches S12 to S18, and grounded via a switch S1G. Likewise, the element seg8a2 is connected to the elements DAS-1a1 to DAS-8a1 and to the ground via switches S21 to S2G.

The element seg4a1 is connected to the elements DAS-1a1 to DAS-8a1 and to the ground via switches S31 to S3G. The element seg4a2 is connected to the elements DAS-1a1 to DAS-8a1 and to the ground via switches S41 to S4G. The element seg2a1 is connected to the elements DAS-1a1 to DAS-8a1 and to the ground via switches S51 to S5G. The element seg2a2 is connected to the elements DAS-1a1 to DAS-8a1 and to the ground via switches S61 to S6G.

The elements seg1a1 to seg1a8 are connected to the elements DAS-1a1 to DAS-8a1 and to the ground via switches S71 to S7G and switches S141 to S14G respectively. The element seg2a3 is connected to the elements DAS-1a1 to DAS-8a1 and to the ground via switches S151 to S15G. The element seg2a4 is connected to the elements DAS-1a1 to DAS-8a1 and to the ground via switches S161 to S16G. The element seg4a3 is connected to the elements DAS-1a1 to DAS-8a1 and to the ground via switches S171 to S17G. The element seg4a4 is connected to the DAS-1a1 to DAS-8a1 and to the ground via switches S181 to S18G.

The elements seg8a3 is connected to the elements DAS-1a1 to DAS-8a1 and to the ground via switches S191 to S19G. The element seg8a4 (twentieth segment) is connected to the elements DAS-1a1 to DAS-8a1 and to the ground via switches S201 to S20G.

Control signal lines that are not shown are routed from a host controller 25 in the system unit 4 to the connection switches S11 to S20G. The connection switches S11 to S20G are mutually-independently turned on or off according to control signals sent from the host controller 25 over the control signal lines. Thus, connection or disconnection of each of the elements seg1a1 to seg1a8, seg2a1 to seg2a4, seg4a1 to seg4a4, and seg8a1 to seg8a4 to or from each of the elements DAS-1a1 to DAS-8a1 and the ground is controlled independently.

The detecting elements belonging to the rows of detecting elements 11a2 to 11a16 constituting the second channel to sixteenth channel are, like those of the row of detecting elements 11a1 constituting the first channel, connected to the associated data acquisition elements DAS-1a2 to DAS-8a2, etc., and DAS-1a16 to DAS-8a16 via connection switches. Each connection switch controls connection or disconnection of each detecting element to or from each data acquisition element of the DAS and the ground according to a control signal sent from the host controller 25.

By the way, the system unit 4 of the X-ray CT scanner 1 includes a data processing unit 26 in which a computer circuit having a CPU and the like is incorporated. The data processing unit 26 retains projection data items of 8 slices acquired by the data acquisition elements of the DAS 21, adds up all the projection data items of the same slice obtained by scanning the subject in multiple directions with the rotation of the gantry 3, and carries out interpolation, correction, or the like on the multi-directional projection data resulting from the addition.

The system unit 4 comprises a memory unit 27 in which data needed for data processing by the data processing unit 26 is stored, a reconstruction unit 28 for reconstructing projection data processed by the data processing unit 26 so as to produce reconstructed image data of 8 slices, a display unit 29 for displaying the reconstructed image data produced by the reconstruction unit 28, an input unit 30 including a keyboard, various switches, mouse, and the like and enabling an operator O to enter various conditions for scanning such as a slice thickness and the number of slices, and an auxiliary memory unit 31 having a large-capacity storage area capable of storing the reconstructed image data produced by the reconstruction unit 28.

The system unit 4 of the X-ray CT scanner 1 includes the host controller 25 in which a computer circuit having a CPU is incorporated. The host controller 25 is connected to the high-voltage generating unit 15, and also connected to the patient couch drive unit, which is not shown, inside the gantry, the gantry drive unit 12, the beam trimmer 14, the group of switches 20, and the DAS 21 respectively over a bus B.

The host controller 25, data processing unit 26, memory unit 27, reconstruction unit 28, display unit 29, input unit 30, and auxiliary memory unit 31 are interconnected over the bus B, and can therefore transfer image data or control data to or from one another over the bus B at a high speed.

In other words, the host controller 25 stores the conditions for scanning such as a slice thickness, which are entered at the input unit 30 by the operator O, in an internal memory. Based on the stored conditions for scanning (or the conditions for scanning designated directly by the operator O in a manual mode), the high-voltage generating unit 15, patient couch drive unit that is not shown, gantry drive unit 12, and beam trimmer 14 are driven while a magnitude of feed of the patient couch 2 in a body-axis direction and a feed speed thereof, a rotating speed of the gantry 3 (X-ray tube 10 and main detector 11) and a rotation pitch thereof, the positions of the edges of a fan beam defined by the beam trimmer 14, and the timing of bombarding X rays are controlled through the high-voltage generating unit 15, patient couch drive unit, gantry drive unit 12, and beam trimmer 14. Thus, a conical X-ray beam is irradiated in multiple directions to a desired scanned region of the subject P. Transmitted X rays passing through the scanned region of the subject P are detected as X-ray transmission data by the detecting elements of the main detector 11.

At the same time, the host controller 25 controls connection or disconnection of each switch of the group of switches 20 on the basis of the conditions for scanning stored in the internal memory (or the conditions for scanning entered in the manual mode) so as to change the connected or disconnected states of the detecting elements of the main detector 11 to the DAS 21. The host controller 25 then combines X-ray transmission data items detected by the detecting elements, and sends resultant data as X-ray transmission data of a plurality of slices that meet the conditions for scanning to the DAS 21.

Next, connection modes for combining X-ray transmission data items using the group of switches 20 in this embodiment will be described. For brevity's sake, only the connections modes for combining X-ray transmission data items detected by the row of detecting elements 11a1 constituting the first channel of the main detector 11, and sending resultant data items to the elements DAS-1a1 to DAS-8a1 are illustrated. Needless to say, the connection modes can also apply to connections between the rows of detecting elements 11a2 to 11a16 constituting the second to sixteenth channels and the elements DAS-1a2 to DAS-8a2 to the elements DAS-1a16 to DAS-8a16.

To begin with, the ways of combining X-ray transmission data items using the group of switches 20 in a data acquisition mode in which data of 8 slices having the same slice thickness is acquired are shown in FIGS. 6 and 7. In FIGS. 6 and 7, a hatched area indicates the range of detecting elements whose detected X-ray transmission data is employed, and a bold line indicates a division of combined X-ray transmission data.

Figure 6A:
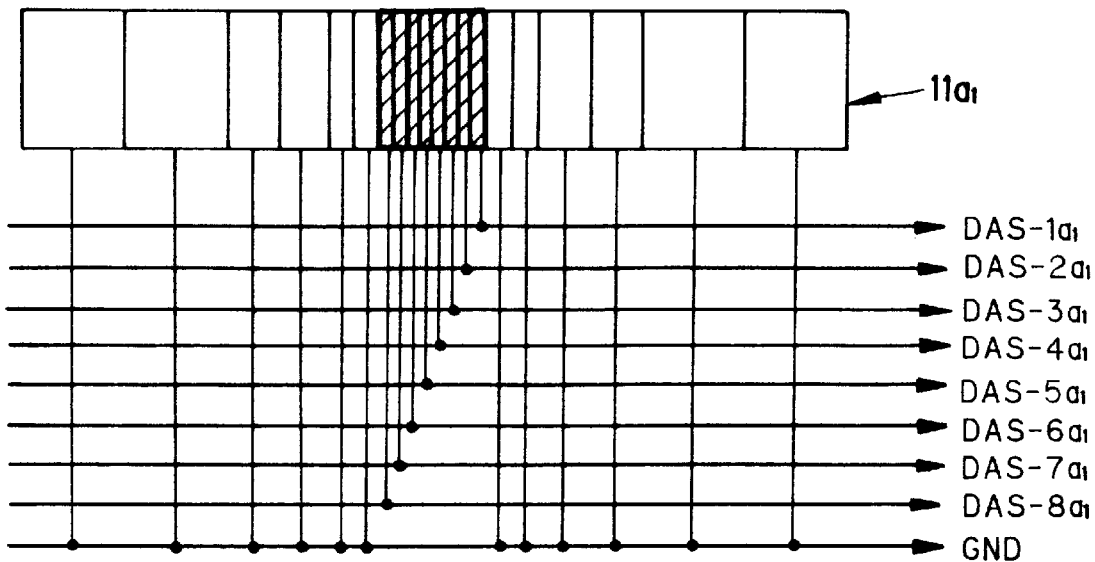
FIGS. 6A and 6B show the way of combining data items in a data acquisition mode in which data of 8 slices having the same pitch relative to adjoining slices is acquired.

FIG. 6A shows the way of combining X-ray transmission data items using the group of switches 20 in a data acquisition mode in which data of 8 slices having a minimum slice thickness (1 mm) is acquired.

To be more specific, the host controller 25 controls the on or off states of the switches S11 to S20G of the group of switches 20 under the conditions for scanning including the input condition of a slice thickness (1 mm), and combines X-ray transmission data items detected by each row of detecting elements. In other words, the switches S71, S82, S93, S104, S115, S126, S137, and S148 for connecting the elements seg1a1 to seg1a8 to the elements DAS-1a1 to DAS-8a1 are turned on, the other switches S72 to S7G, S81, S83 to S8G, S91, S92, S94 to S9G, etc., S141 to S147, and S14G are turned off.

The switches S1G, S2G, S19G, and S20G for connecting the elements seg8a1 to seg8a4 to the ground are turned on. The switches S3G, S4G, S17G, and S18G for connecting the elements seg4a1 to seg4a4 to the ground are turned on, and the switches S5G, S6G, S15G, and S16G for connecting the elements seg2a1 to seg2a4 to the ground are turned on. The switches S11 to S18, S21 to S28, S31 to S38, etc., S61 to S68, S151 to S158, S161 to S168, etc., and S201 to S208 are turned off.

Consequently, X-ray transmission data of 8 slices having a slice thickness of 1 mm can be sent as detected data provided by the row of detecting elements 11a1 constituting the first channel to the elements DAS-1a1 to DAS-8a1.

Figure 6B:
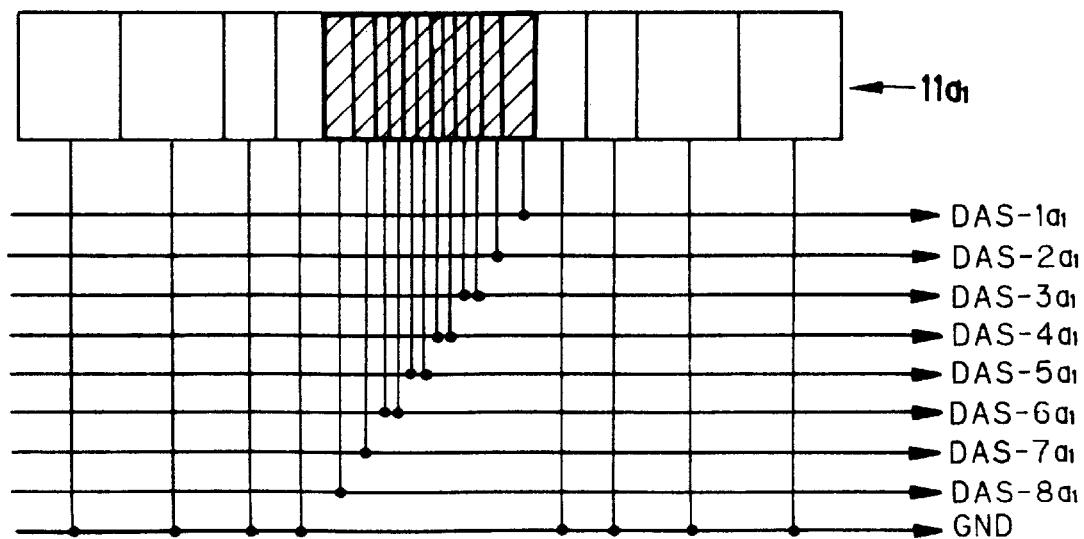

FIG. 6B shows the way of combining X-ray transmission data items using the group of switches 20 in a data acquisition mode in which data of 8 slices having a slice thickness of 2 mm is acquired.

To be more specific, the host controller 25 controls the on or off states of the switches S11 to S20G of the group of switches 20 under the conditions for scanning including the input condition of a slice thickness (2 mm), connects the element seg2a1 to the element DAS-1a1 and the element seg2a2 to the element DAS-2a1, combines the elements seg 1a1 and seg1a2 and connects them to the element DAS-3a1, combines the elements seg1a3 and seg1a4 and connects them to the DAS-4a1, combines the elements seg1a5 and seg1a6 and connects them to the element DAS-5a1, and combines the elements seg1a7 and seg1a8 and connects them to the element DAS-6a1. Moreover, the element seg2a3 is connected to the element DAS-7a1, and the element seg2a4 is connected to the element DAS-8a1. All the other elements seg4a1 to seg4a4 and seg8a1 to seg8a4 are grounded. Consequently, X-ray transmission data of 8 slices having a thickness of 2 mm can be sent as detected data provided by the row of detecting elements 11a1 constituting the first channel to the elements DAS-1a1 to DAS-8a1.

Figure 7A:
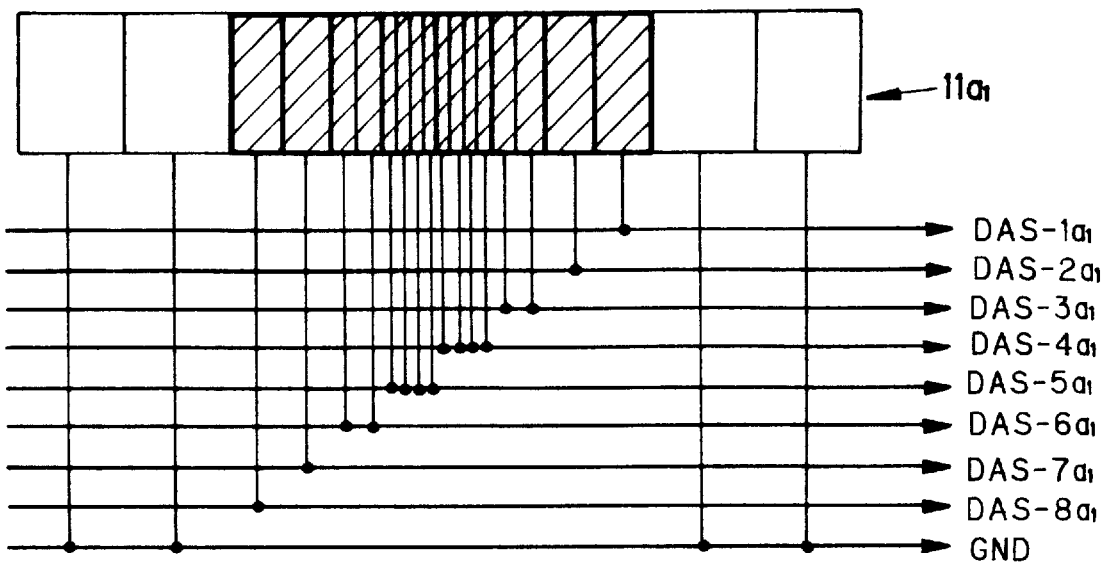
FIGS. 7A and 7B show the way of combining data items in a data acquisition mode in which data of 8 slices having the same pitch relative to adjoining slices is acquired.

Likewise, in FIG. 7A, the host controller 25 controls the on or off states of the switches S11 to S20G, and thus connects the element seg4a1 to the element DAS-1a1, the element seg4a2 to the element DAS-2a1, the elements seg2a1 and seg2a2 to the element DAS-3a1, the elements seg1a1 and seg1a4 to the element DAS-4a1, the elements seg1a5 to seg1a8 to the element DAS-5a1, the elements seg2a3 and seg2a4 to the element DAS-6a1, the element seg4a3 to the element DAS-7a1, the element seg4a4 to the element DAS-8a1, and the elements seg8a1 to seg8a4 to the ground respectively. Consequently, X-ray transmission data of 8 slices having a thickness of 4 mm can be sent as detected data provided by the row of detecting elements 11a1 constituting the first channel to the elements DAS-1a1 to DAS-8a1.

Figure 7B:
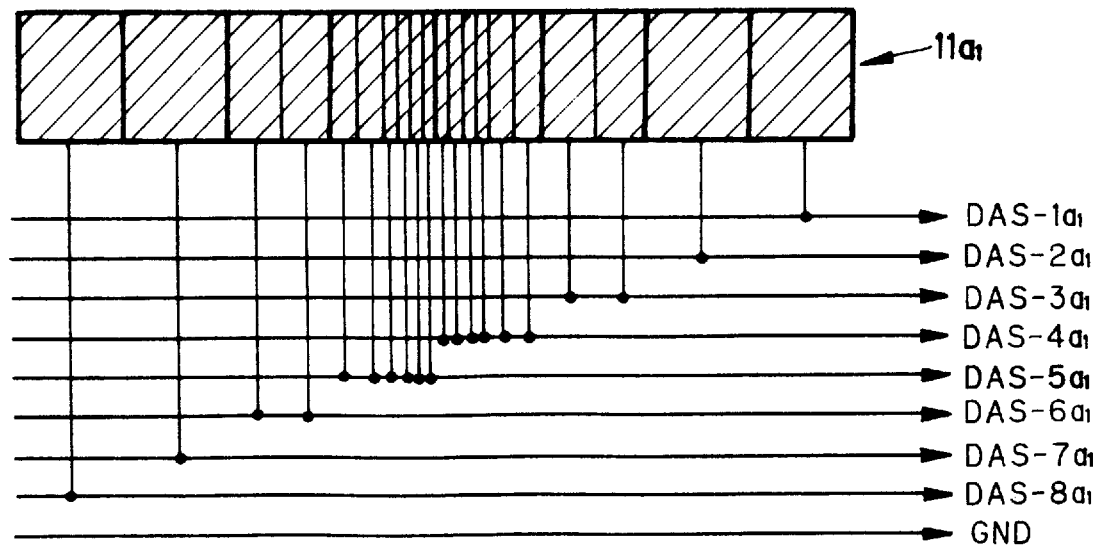

In FIG. 7B, the on or off states of the switches S11 to S20G are controlled in order to connect the element seg8a1 to the element DAS-1a1, the element seg8a2 to the element DAS-2a1, the elements seg4a1 and seg4a2 to the element DAS-3a1, the elements seg2a1 and seg2a2 and the elements seg1a1 to seg1a4 to the element DAS-4a1, the elements seg1a5 to seg1a8 and the elements seg2a3 and seg2a4 to the element DAS-5a1, the elements seg4a3 and seg4a4 to the element DAS-6a1, the element seg8a3 to the element DAS-7a1, and the element seg8a4 to the element DAS-8a1. Consequently, X-ray transmission data of 8 slices having a slice thickness of 8 mm can be sent as detected data provided by the row of detecting elements 11a1 constituting the first channel to the elements DAS-1a1 to DAS-8a1.

As mentioned above, according to this embodiment, in a data acquisition mode in which X-ray transmission data of 8 slices having the same slice thickness is acquired, the slice thickness can be continuously doubled to be 2 mm, 4 mm, and 8 mm.

Any of the slice thicknesses is selected according to the conditions for scanning (the condition of a slice thickness) by automatically controlling connection or disconnection of the group of switches 20 under the control of the host controller 25 on the basis of a slice thickness included in the conditions for scanning designated by the operator O.

Specifically, according to this embodiment, X-ray transmission data of 8 slices having a minimum slice thickness (1 mm) can be acquired under the designated condition of a slice thickness. Based on projection data stemming from the acquired X-ray transmission data of 8 slices, the reconstruction unit 28 carries out reconstruction. This results in reconstructed images of 8 slices having high resolving power (resolution) in a body-axis direction. Moreover, X-ray transmission data of a wide scanned region (64 mm) defined with 8 slices having a slice thickness of, for example, 8 mm can be acquired under the designated condition of a slice thickness. The reconstruction unit 28 then carries out image reconstruction on the basis of projection data stemming from the acquired X-ray transmission data. Consequently, a reconstructed image of the wide range in the body-axis direction can be produced. In this embodiment, therefore, both high resolution in the body-axis direction and a wide scanned region therein can be realized.

Moreover, according to this embodiment, when projection data of 8 slices having the same slice thickness is acquired, a value to be set as the slice thickness can be doubled to be 1 mm, 2 mm, 4 mm, and 8 mm according to the designated condition of a slice thickness. Moreover, the condition of a slice thickness can be designated arbitrarily by the operator O at the time of designating the conditions for scanning or in a manual mode. Consequently, the freedom in designating a slice thickness can be increased greatly, and image diagnosis can be achieved efficiently according to a diagnostic region.

Next, the procedures of combining X-ray transmission data items using the group of switches 20 in a data acquisition mode in which data of 8 slices having different (unequal) slice thicknesses is acquired are shown in FIGS. 8A to 9B. In FIGS. 8A to 9B, like FIGS. 6A to 7B, a hatched area indicates a range of detecting elements whose detected X-ray transmission data is employed, and a bold line indicates a division of combined X-ray transmission data.

In FIGS. 8A to 9B, the center of the columns of the detector is used to acquire data of thin slices, and the outer columns thereof are used to acquire data of thick slices.

Figure 8A:
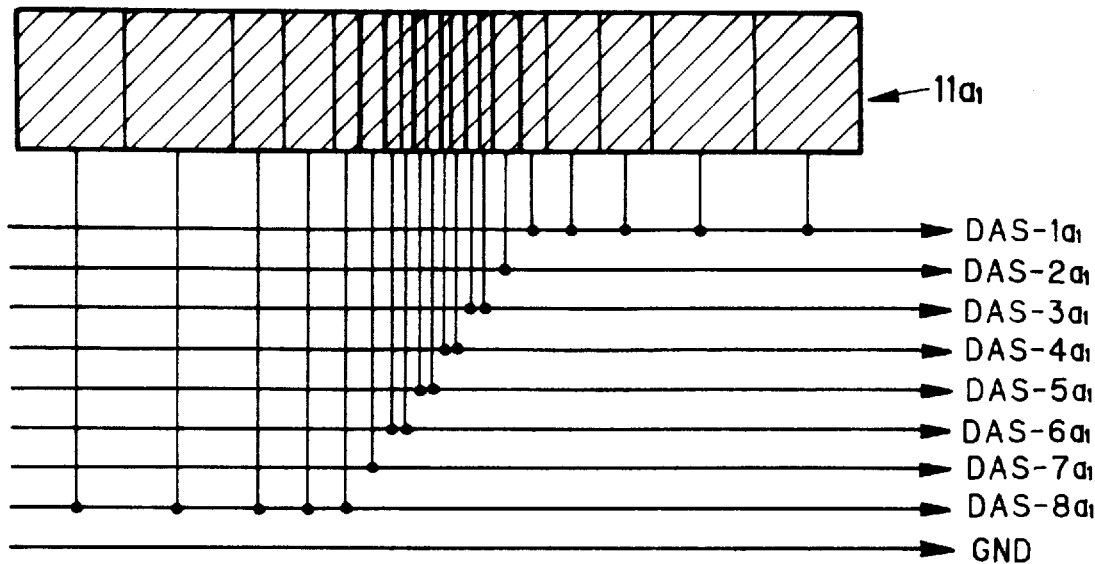
FIGS. 8A and 8B show the way of combining data items in a data acquisition mode in which data of 8 slices having different pitches relative to adjoining slices is acquired.

Specifically, in FIG. 8A, with the on-off control of the group of switches 20 under the control of the host controller 25, the elements seg8a1 and seg8a2, seg4a1 and seg4a2, and seg2a1 (defining a slice having a total thickness of 26 mm) are connected to the element DAS-1a1, the element seg2a2 is connected to the element DAS-2a1, the elements seg1a1 and seg1a2 are connected to the element DAS-3a1, the elements seg1a3 and seg1a4 are connected to the element DAS-4a1, the elements seg1a5 and seg1a6 are connected to the element DAS-5a1, and the elements seg1a7 and seg1a8 are connected to the element DAS-6a1. Moreover, the element seg2a3 is connected to the element DAS-7a1, the elements seg8a3 and seg8a4, seg4a3 and seg4a4, and seg2a4 (defining a slice having a total thickness of 26 mm) are connected to the element DAS-8a1.

As a result, X-ray transmission data of 8 slices having different slice thicknesses; such as, a slice of 26 mm thick, six slices of 2 mm thick, and a slice of 26 mm thick can be sent to the elements DAS-1a1 to DAS8a1.

Figure 8B:
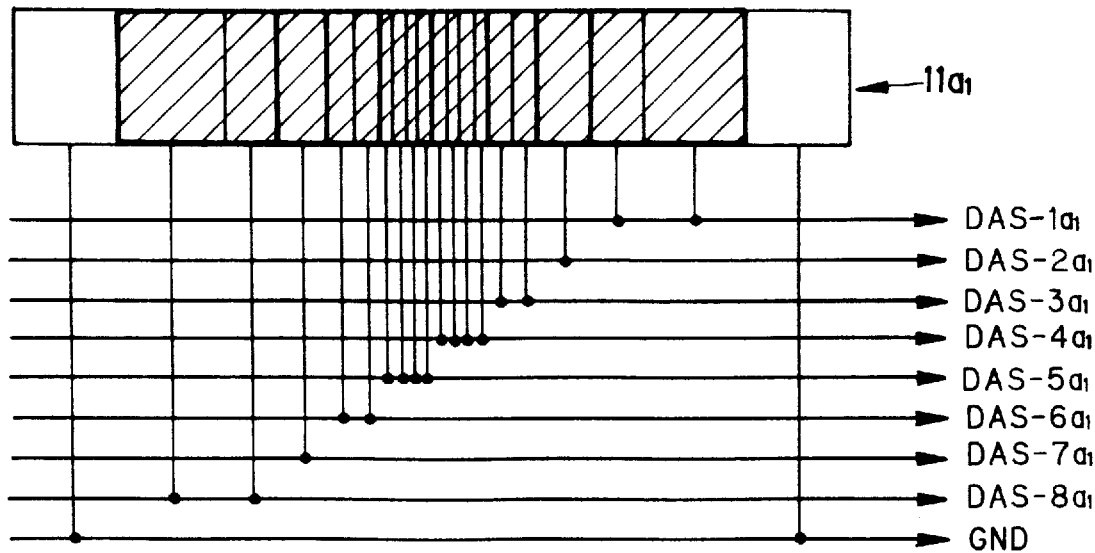

Referring to FIG. 8B, with the on-off control of the group of switches 20 under the control of the host controller 25, the element seg8a1 is grounded, the elements seg8a2 and seg4a1 are connected to the DAS-1a1, the element seg4a2 is connected to the element DAS-2a1, the elements seg2a1 and seg2a2 are connected to the element DAS-3a1, the elements seg1a1 to seg1a4 are connected to the element DAS-4a1. The elements seg1a5 to seg1a8 are connected to the element DAS-5a1, the segments seg2a3 and seg2a4 are connected to the DAS-6a1, the element seg4a3 is connected to the element DAS-7a1, the elements seg4a4 and seg8a3 are connected to the element DAS-8a1, and the element seg8a4 is grounded.

As a result, X-ray transmission data of 8 slices having different slice thicknesses, that is, a slice of 12 mm thick, six slices of 4 mm thick, and a slice of 12 mm thick can be sent to the elements DAS-1a1 to DAS-8a1.

Figure 9A:
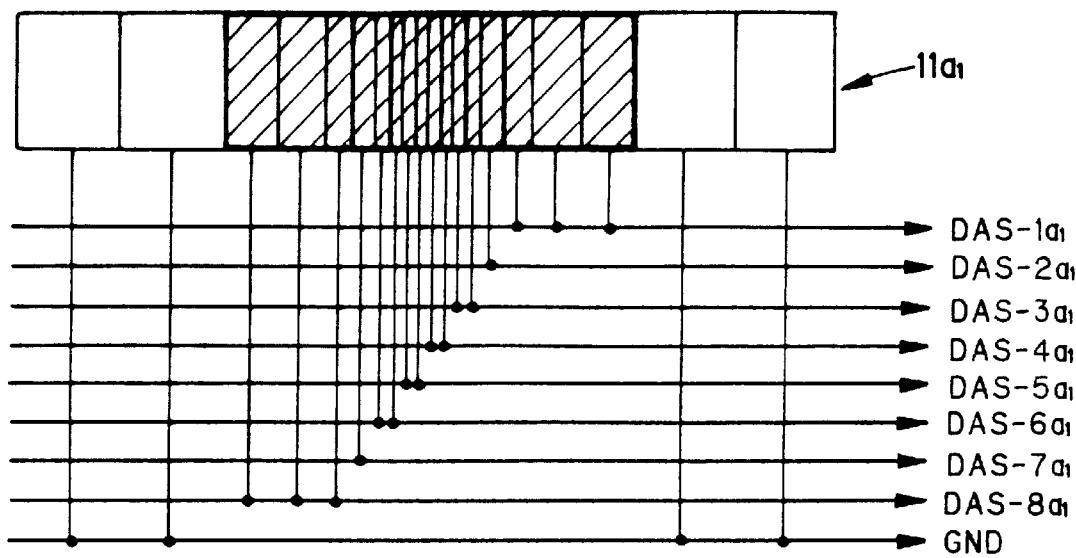
FIGS. 9A and 9B show the way of combining data items in a data acquisition mode in which data of 8 slices having different pitches relative to adjoining slices is acquired.

Likewise, referring to FIG. 9A, with the on-off control of the group of switches 20 under the control of the host controller 25, the elements seg8a1 and seg8a2 are grounded, the elements seg4a1 and seg4a2 and the element seg2a1 are connected to the element DAS-1a1, the element seg2a2 is connected to the element DAS-2a1, the elements seg 1a1 and seg1a2 are connected to the element DAS-3a1, and the elements seg1a3 and seg1a4 are connected to the element DAS-4a1. Moreover, the elements seg1a5 and seg1a6 are connected to the element DAS-5a1, the elements seg1a7 and seg1a8 are connected to the element DAS-6a1, the element seg2a3 is connected to the element DAS-7a1, the elements seg2a4 and the elements seg4a3 and seg4a4 are connected to the element DAS-8a1, and the elements seg8a3 and seg8a4 are grounded. As a result, X-ray transmission data of 8 slices having different slice thicknesses, that is, a slice of 10 mm thick, six slices of 2 mm thick, and a slice of 10 mm thick can be sent to the elements DAS-11a1 to DAS-8a1.

Figure 9B:
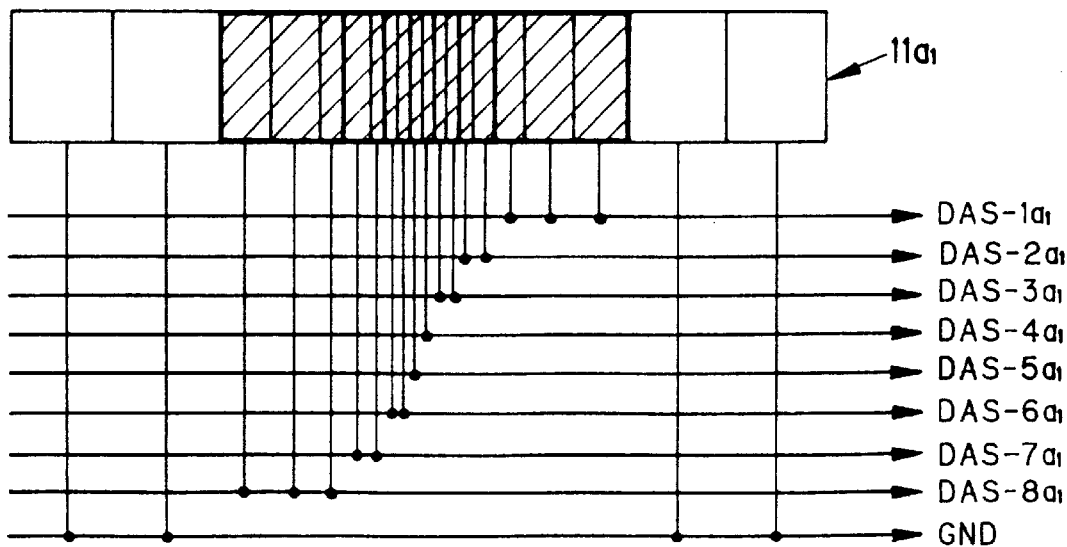

Referring to FIG. 9B, the elements seg8a1 and seg8a2 are grounded, the elements seg4a1 and seg4a2 and the element seg2a1 are connected to the element DAS-1a1, the elements seg2a2 and seg1a1 are connected to the element DAS-2a1, the elements seg1a2 and seg1a3 are connected to the element DAS-3a1, and the element seg1a4 is connected to the element DAS-4a1. Moreover, the element seg1a5 is connected to the element DAS-5a1, the elements seg1a6 and seg1a7 are connected to the element DAS-6a1, the element seg1a8 and seg2a3 are connected to the element DAS-7a1, the element seg2a4 and the elements seg4a3 and seg4a4 are connected to the element DAS-8a1, and the elements seg8a3 and seg8a4 are grounded. As a result, X-ray transmission data of 8 slices having different slice thicknesses, that is, a slice of 10 mm thick, a slice of 3 mm thick, a slice of 2 mm thick, a slice of 1 mm thick, a slice of 1 mm thick, a slice of 2 mm thick, a slice of 3 mm thick, and a slice of 10 mm thick can be sent to the elements DAS-1a1 to DAS-8a1.

As mentioned above, according to this embodiment, projection data of 8 slices having not only the same slice thickness but also different slice thicknesses can be acquired. The freedom in designating a slice thickness can be further expanded, and image diagnosis can be achieved efficiently according to a diagnostic region.

In FIGS. 8A to 9B, the center of the columns of the detector is used to detect data of thin slices, and the outer columns thereof are used to detect data of thick slices. Alternatively, the center part may be associated with thick slices. Anyhow, various slice thicknesses can be set according to a diagnostic region.

The description of the aforesaid connection modes has proceeded by taking for instance a data acquisition mode in which X-ray transmission data detected by the main detector 11, in which a total of 20 segments whose widths range from 1 mm to 8 mm are arranged to constitute each channel, is acquired as projection data by the DAS 21 that includes data acquisition elements numbering a multiple of 8 slices. The rules on the relationship between the number of data acquisition elements of the DAS and the number of segments belonging to a row of detecting elements will be described.

As apparent from the description of the connection modes, for setting a slice thickness, which is realized by combining segments using the group of switches 20, to a value that is $2^k$ (1, 2, 4, 8, etc.) times as large as a reference slice thickness, the DAS 21 should preferably include data acquisition elements numbering a product of "4 by n slices (where n is a natural number)" per row of detecting elements constituting each channel. The segments belonging to each row of detecting elements of the main detector 11 are arranged in such a way that reference segments numbering a product of 4 by n are laid out in the center, segments numbering a product of 2 by n in total and each having a width that is twice as large as the width of each reference segment are laid out on both outer sides of the reference segments by arranging n segments on each side, segments numbering a product of 2 by n in total and each having a width that is twice as large as the width of each of the preceding segments (four times as large as the width of each reference segment) are laid out on both sides of the preceding segments by arranging n segments on each side, and so on.

Figure 10:
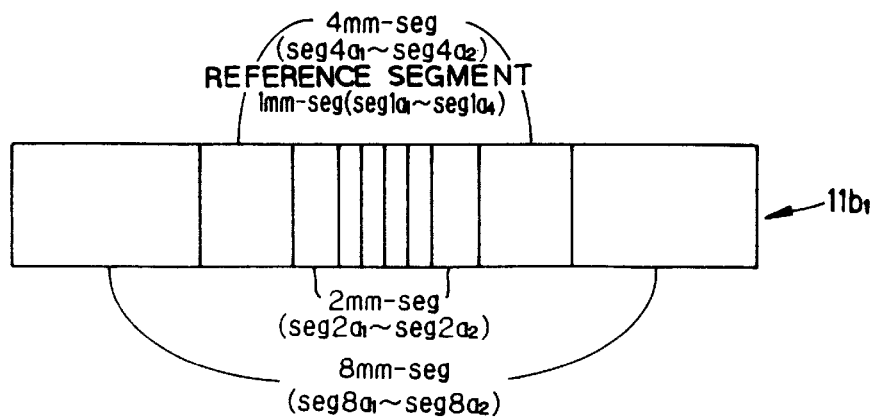
FIG. 10 is a diagram showing an example of the structure of a row of detecting elements in such a connection mode that a DAS designed for handling 4 slices is used to acquire data.

The structure of a row of detecting elements constituting the first channel of the main detector 11 shown in FIG. 3 is realized in case of "n=2." FIG. 10 shows another example of the structure of a row of detecting elements 11b1 constituting the first channel, wherein "n=1" is established (there are elements DAS1a1 to DAS-4a1 for handling 4 slices). The same applies to the other rows of detecting elements 11b2 to 11b16.

Referring to FIG. 10, 4 reference segments (seg1a1 to seg1a4) of 1 mm wide are laid out in the center, a total of 2 segments of 2 mm wide (seg2a1 and seg2a2) are arranged one by one on both outer sides of the reference segments, a total of 2 segments of 4 mm wide (seg4a1 to seg4a2) are arranged one by one on both outer sides of the segments of 2 mm wide, and a total of 2 segments of 8 mm wide (seg8a1 to seg8a2) are laid out one by one on both outer sides of the segments of 4 mm wide. A total of 10 segments are defined per channel, coming to 32 mm in width.

The ways of combining X-ray transmission data detected by the row of detecting elements 11b1 using the group of switches 20 (for acquiring data of 4 slices having the same slice thickness) are shown in FIGS. 11A to 12B. Like FIGS. 6A to 7B, a hatched area indicates a range of detecting elements, X-ray transmission data detected by which is employed, and a bold line indicates a division of combined X-ray transmission data.

Figure 11A:
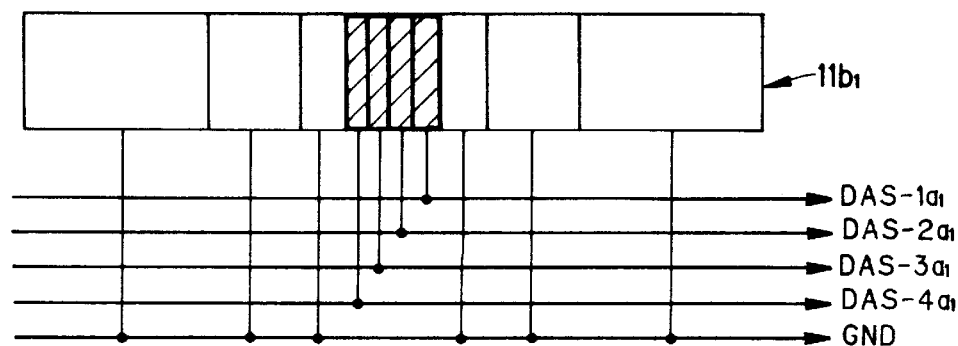
FIGS. 11A and 11B show the way of combining data items in a data acquisition mode in which data of 4 slices having the same pitch relative to adjoining slices is acquired.

Referring to FIG. 11A, like FIGS. 6A and 7A, with the on-off control of the switches, which are not shown, by the controller 25, the elements seg8a1, seg4a1, and seg2a1 are grounded, the element seg1a1 is connected to the element DAS-1a1, the element seg1a2 is connected to the element DAS-2a1, the element seg1a3 is connected to the element DAS-3a1, the element seg1a4 is connected to the element DAS-4a1, and the elements seg2a2, seg4a2, and seg8a2 are grounded. Thus, X-ray transmission data of 4 slices having a slice thickness of 1 mm can be sent to the elements DAS-1a1 to DAS-4a1.

Figure 11B:
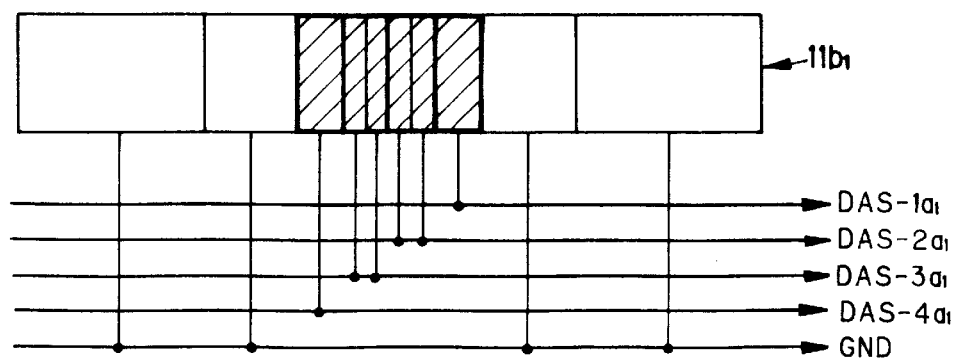

Referring to FIG. 11B, the elements seg8a1 and seg4a1 are grounded, the element seg2a1 is connected to the element DAS-1a1, the elements seg1a1 and seg1a2 are connected to the element DAS-2a1, the elements seg1a3 and seg1a4 are connected to the element DAS-3a1, the element seg2a2 is connected to the element DAS-4a1, and the elements seg4a2 and seg8a2 are grounded. Thus, X-ray transmission data of 4 slices having a slice thickness of 2 mm can be sent to the elements DAS-1a1 to DAS-4a1.

Figure 12A:
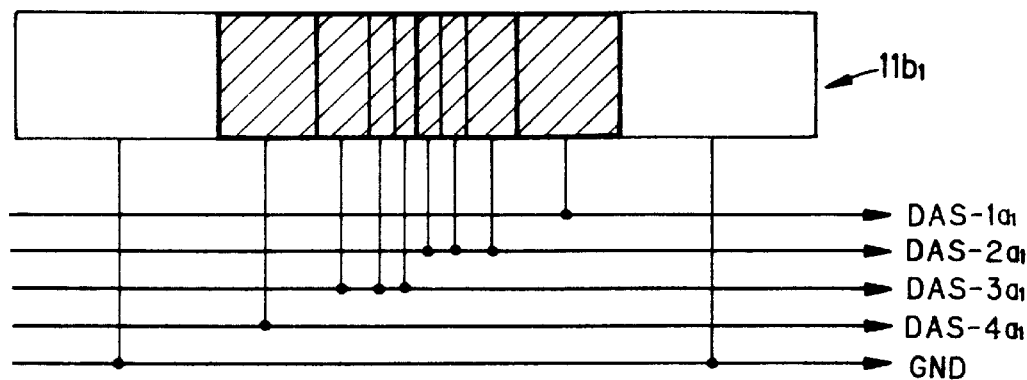
FIGS. 12A and 12B show the way of combining data items in a data acquisition mode in which data of 4 slices having the same pitch relative to adjoining slices is acquired.
Figure 12B:
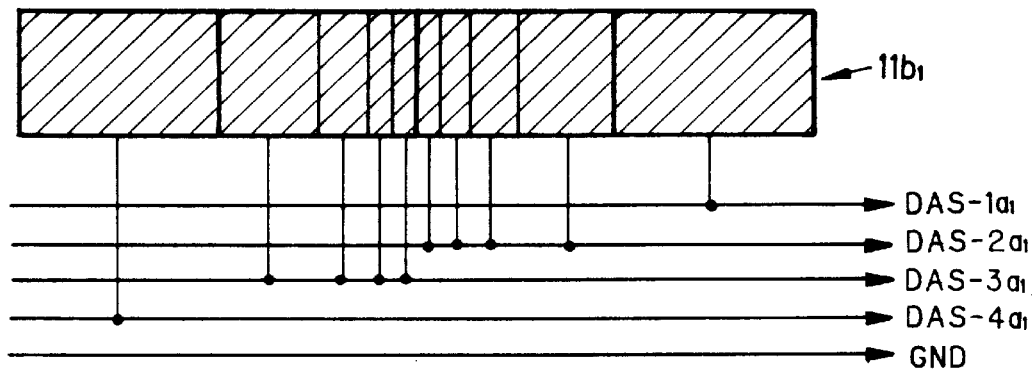

Referring to FIG. 12A, the element seg8a1 is grounded, the element seg4a1 is connected to the element DAS-1a1, the elements seg2a1 and the elements seg1a1 and seg1a2 are connected to the element DAS-2a1, the elements seg1a3 and seg1a4 and the element seg2a2 are connected to the element DAS-3a1, the element seg4a2 is connected to the element DAS-4a1, and the element seg8a2 is grounded. Thus, X-ray transmission data of 4 slices having a slice thickness of 4 mm can be sent to the elements DAS-1a1 to DAS-4a1. Referring to FIG. 12B, the element seg8a1 is connected to the element DAS-1a1, the elements seg4a1 and seg2a1 and the elements seg1a1 and seg1a2 are connected to the element DAS-2a1, the elements seg1a3 and seg1a4 and the elements seg2a1 and seg4a2 are connected to the element DAS-3a1, and the element seg8a2 is connected to the element DAS-4a1. Thus, X-ray transmission data of 4 slices having a slice thickness of 8 mm can be sent to the elements DAS-1a1 to DAS-4a1.

Even when the DAS 21 includes data acquisition elements numbering a product of "2 by (2n−1) slices," the same structure as the aforesaid structure of the row of detecting elements 11a composed of detecting elements numbering a product of "4 by n slices" is adopted. FIGS. 13A to 14B show the ways of combining the detecting elements belonging to the row of detecting elements 11a having a structure defined with "n=2" (there are elements DAS-1a1 to DAS-6a1 for handling 6 slices). The structure of the row of detecting elements 11a is identical to the structure of the row of detecting elements 11a (See FIG. 3) adopted in the connection mode in which a DAS designed for handling 8 slices is employed. However, the way of combining the detecting elements is different.

Figure 13A:
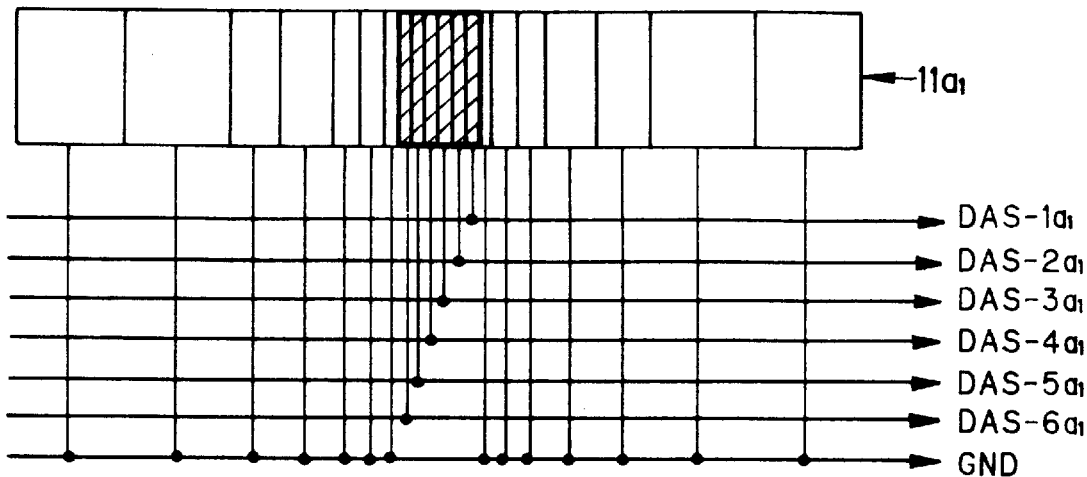
FIGS. 13A and 13B show the way of combining data items in a data acquisition mode in which data of 6 slices having the same pitch relative to adjoining slices is acquired with the pitch doubled.

Specifically, referring to FIG. 13A, the elements seg1a2 to seg1a7 are connected successively to the elements DAS-1a1 to DAS-6a1. The other elements seg1a1 and seg1a8, seg2a1 to seg2a4, etc., and seg8a1 to seg8a4 are all grounded. Thus, X-ray transmission data of 6 slices having a slice thickness of 1 mm can be sent to the elements DAS-1a1 to DAS-6a1.

Figure 13B:
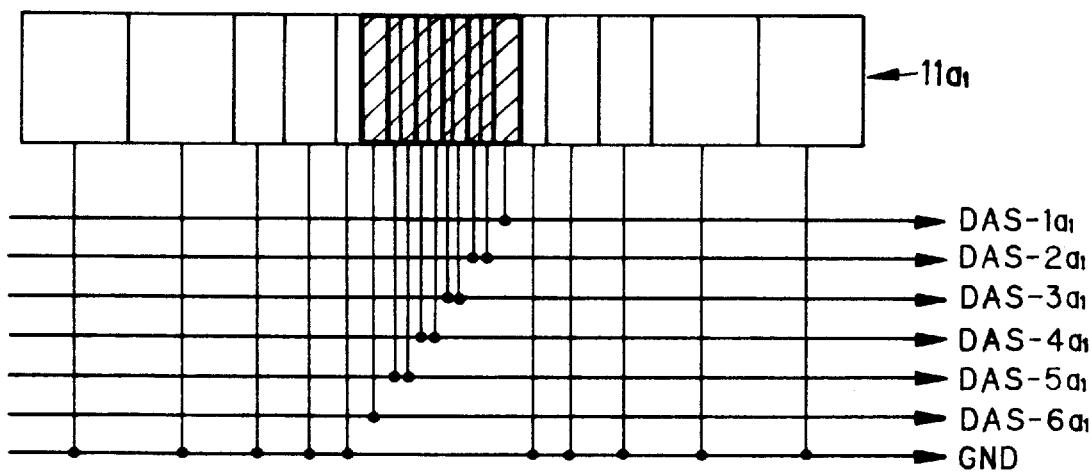

Referring to FIG. 13B, the element seg2a2 is connected to the element DAS-1a1, the elements seg1a1 and seg1a2 are connected to the element DAS-2a1, the elements seg1a3 and seg1a4 are connected to the element DAS-3a1, the elements seg1a5 and seg1a6 are connected to the element DAS-4a1, and the elements seg1a7 and seg1a8 are connected to the element DAS-5a1. The element seg2a3 is connected to the element DAS-6a1, and the other elements seg4a1 to seg4a4, etc., and seg8a1 to seg8a4 are all grounded. Thus, X-ray transmission data of 6 slices having a slice thickness of 2 mm can be sent to the elements DAS-1a1 to DAS-6a1.

Figure 14A:
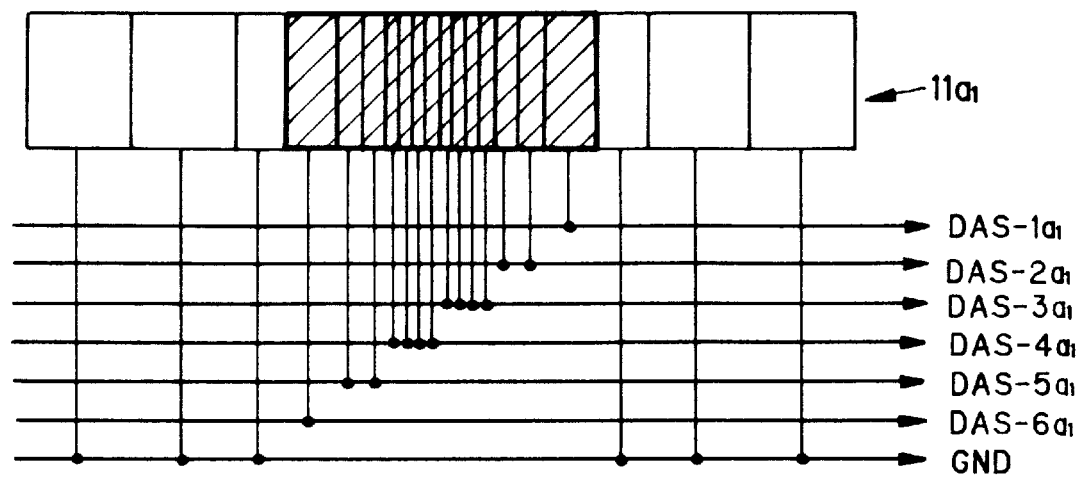
FIGS. 14A and 14B show the way of combining data items in a data acquisition mode in which data of 6 slices having the same pitch relative to adjoining slices is acquired with the pitch doubled.

Likewise, in FIG. 14A, the element seg4a2 is connected to the element DAS-1a1, the elements seg2a1 and seg2a2 are connected to the element DAS-2a1, the elements seg1a1 to seg1a4 are connected to the element DAS-3a1, the elements seg1a5 to seg1a8 are connected to the element DAS-4a1, the elements seg2a3 and seg2a4 are connected to the element DAS-5a1, the element seg4a3 is connected to the element DAS-6a1, and the elements seg4a1 and seg4a4 and the elements seg8a1 to seg8a4 are grounded. Thus, X-ray transmission data of 6 slices having a slice thickness of 4 mm can be sent to the elements DAS-1a1 to DAS-6a1.

Figure 14B:
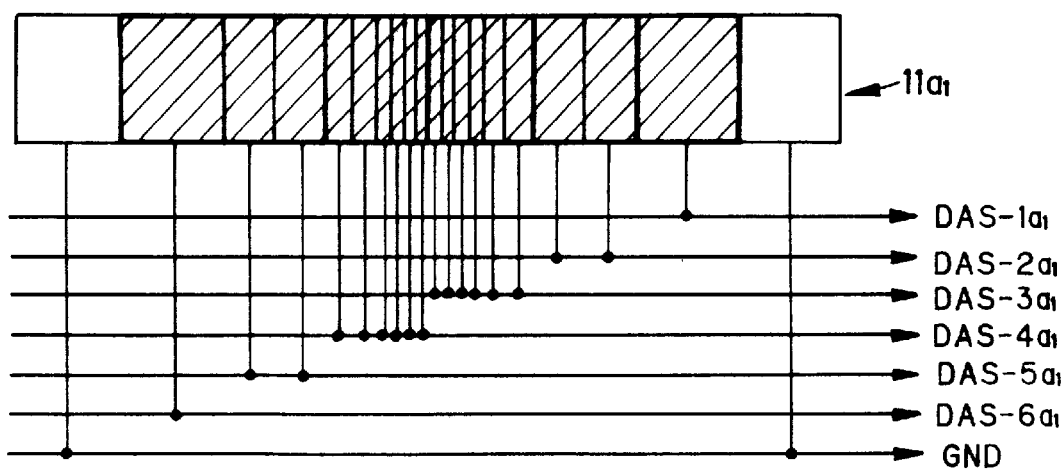

In FIG. 14B, the element seg8a2 is connected to the element DAS-1a1, the elements seg4a1 and seg4a2 are connected to the element DAS-2a1, the elements seg2a1 and seg2a2 and the elements seg1a1 to seg1a4 are connected to the element DAS-3a1, the elements seg1a5 to seg1a8 and the elements seg2a3 and seg2a4 are connected to the element DAS-4a1, the elements seg4a3 and seg4a4 are connected to the element DAS-5a1, the element seg8a3 is connected to the element DAS-6a1, and the elements seg8a1 and seg8a4 are grounded. Thus, X-ray transmission data of 6 slices having a slice thickness of 8 mm can be sent to the elements DAS-1a1 to DAS-6a1.

For setting a slice thickness, which is realized by combining detecting elements using the group of switches 20, to a value that is $3^k$ (1, 3, 9, etc.) times as large as a reference slice thickness, the DAS 21 should preferably include data acquisition elements numbering a product of "3 by n slices (where n is a natural number)." In this case, the segments of the main detector 11 are arranged in such a fashion that reference segments numbering a product of 3 by n are laid out in the center, segments numbering a product of 2 by n in total and having a width that is three times as large as the width of each of the reference segments are laid out on both outer sides of the reference segments by placing n segments on each side, segments numbering a product of 2 by n in total and having a width that is three times as large as that of each of the preceding segments (nine times as large as that of each of the reference segments) are laid out on both outer sides of the preceding segments by placing n segments on each side, and so on.

Figure 15:
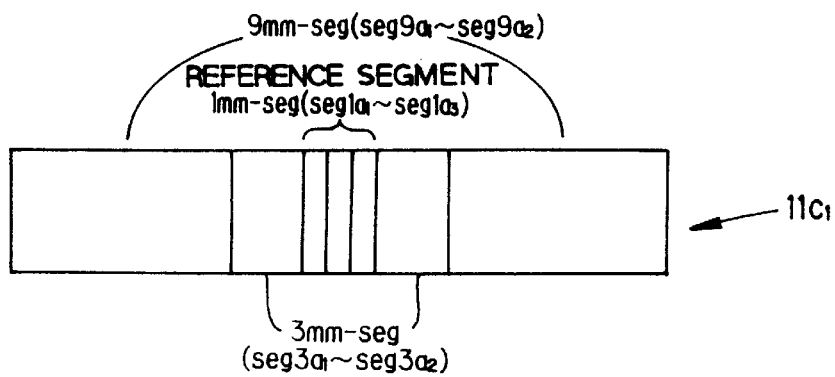
FIG. 15 shows an example of the structure of a row of detecting elements in such a connection mode that a DAS designed for handling data of 3 slices is used to acquire data of slices with the pitch of the slices relative to adjoining slices tripled.

FIG. 15 shows the structure of a row of detecting elements 11c1 constituting the first channel which is defined with "n=1" (there are data acquisition elements (DAS-1a1 to DAS-3a1) for handling three slices).

Referring to FIG. 15, 3 reference segments of 1 mm wide (seg1a1 to seg1a3) are laid out in the center, a total of 2 segments of 3 mm wide (seg3a1 and seg3a2) are laid out one by one on both outer sides of the reference segments, and a total of 2 segments of 9 mm thick (seg9a1 and seg9a2) are laid out one by one on both outer sides of the segments of 3 mm thick. There are a total of 7 segments per channel, coming to 27 mm in width.

Figure 16A:
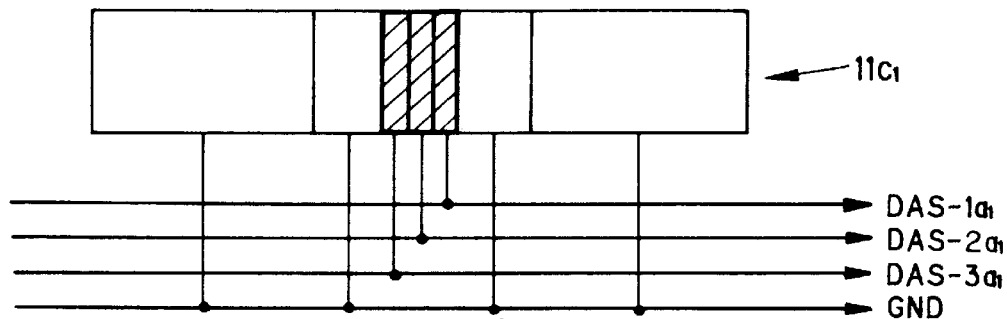
FIGS. 16A to 16C show the way of combining data items in a data acquisition mode in which data of 3 slices having the same pitch relative to adjoining slice is acquired with the pitch tripled.
Figure 16B:
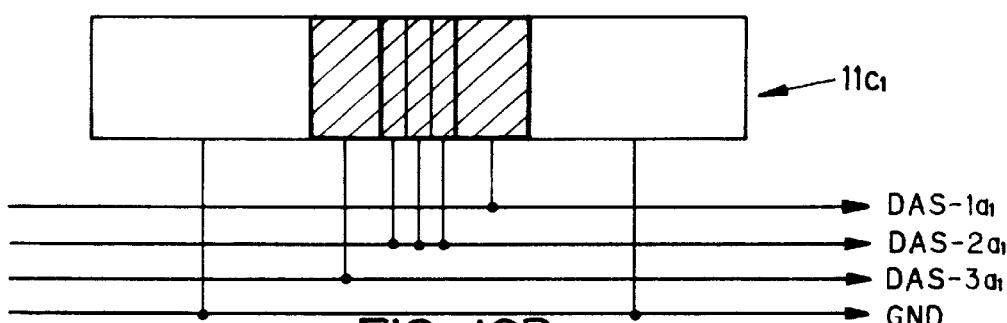
Figure 16C:
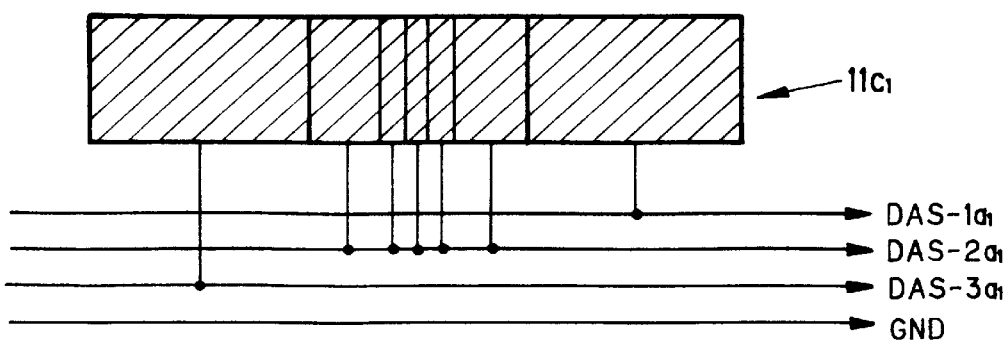

FIGS. 16A to 16C show the ways of combining X-ray transmission data detected by the row of detecting elements 11c1 using the group of switches 20 (for acquiring data of 3 slices having the same slice thickness).

Referring to FIG. 16A, the elements seg9a1 and seg3a1 are grounded, the element seg1a1 is connected to the element DAS-1a1, the element seg1a2 is connected to the element DAS-2a1, the element seg1a3 is connected to the element DAS-3a1, and the elements seg3a2 and seg9a1 are grounded. Thus, X-ray transmission data of 3 slices having a slice thickness of 1 mm can be sent to the elements DAS-1a1 to DAS-3a1.

Referring to FIG. 16B, the element seg9a1 is grounded, the element seg3a1 is connected to the element DAS-1a1, the elements seg1a1 to seg1a3 are connected to the element DAS-2a1, the segment seg3a2 is connected to the element DAS-3a1, and the segment seg9a2 is grounded. Thus, X-ray transmission data of 3 slices having a slice thickness of 3 mm can be sent to the elements DAS-1a1 to DAS-3a1.

Referring to FIG. 16C, the element seg9a1 is connected to the element DAS-1a1, the elements seg3a1, the elements seg1a1 to seg1a3, and the element seg3a2 are connected to the element DAS-2a1, and the element seg9a2 is connected to the element DAS-3a1. Thus, X-ray transmission data of 3 slices having a slice thickness of 9 mm can be sent to the elements DAS-1a1 to DAS-3a1.

Figure 17:
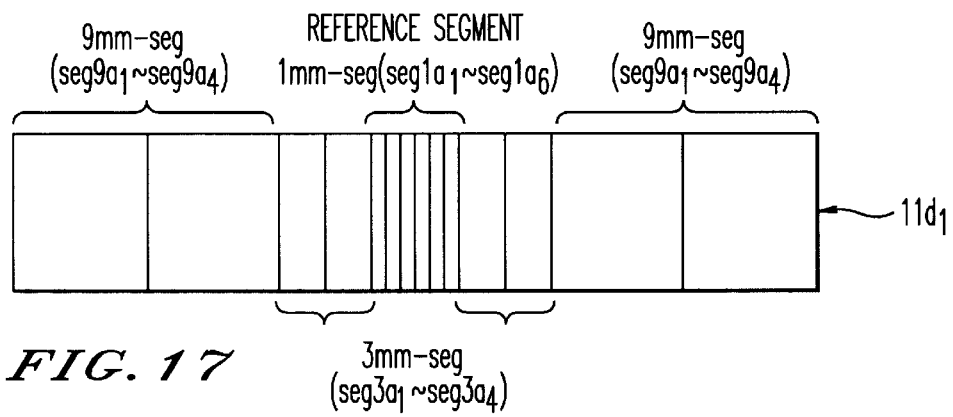
FIG. 17 is a diagram showing an example of the structure of a row of detecting elements in such a connection mode that a DAS designed for handling 6 slices is used to acquire data of slices with the pitch of the slices relative to adjoining slices tripled.

FIG. 17 shows the structure of a row od detecting elements 11d1 constituting the first channel which is defined with "n=2" (there are data acquisition elements DAS-1a1 to DAS-6a1 for handling 6 slices).

Referring to FIG. 17, 6 reference segments of 1 mm wide (seg1a1 to seg1a6) are laid out in the center, a total of 4 segments of 3 mm wide (seg3a1 to seg3a4) are laid out in twos on both outer sides of the reference segments, and a total of 4 segments of 9 mm wide (seg9a1 to seg9a4) are laid out in twos on both outer sides of the segments of 3 mm wide. Thus, there are a total of 14 segments per row coming to 54 mm in width.

Figure 18A:
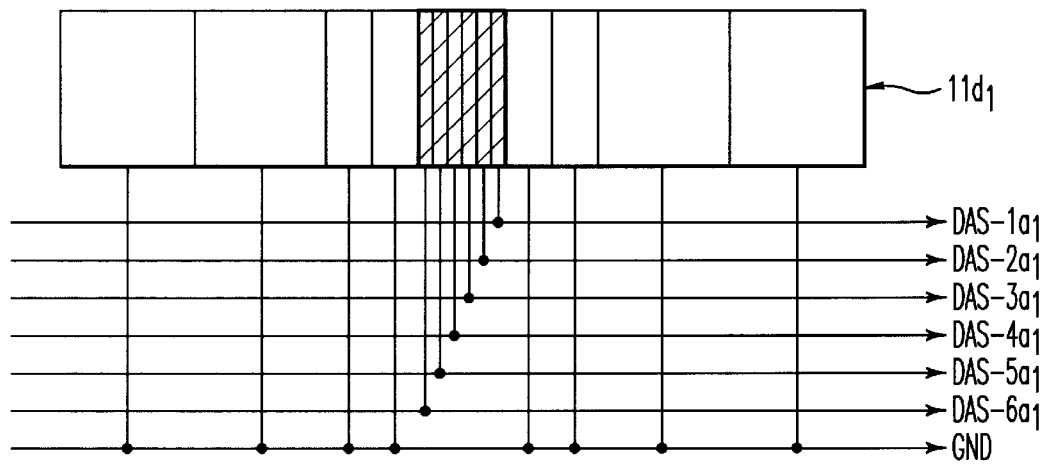
FIGS. 18A and 18B show the way of combining data items in a data acquisition mode in which data of 6 slices having the same pitch relative to adjoining slices is acquired with the pitch tripled.
Figure 18B:
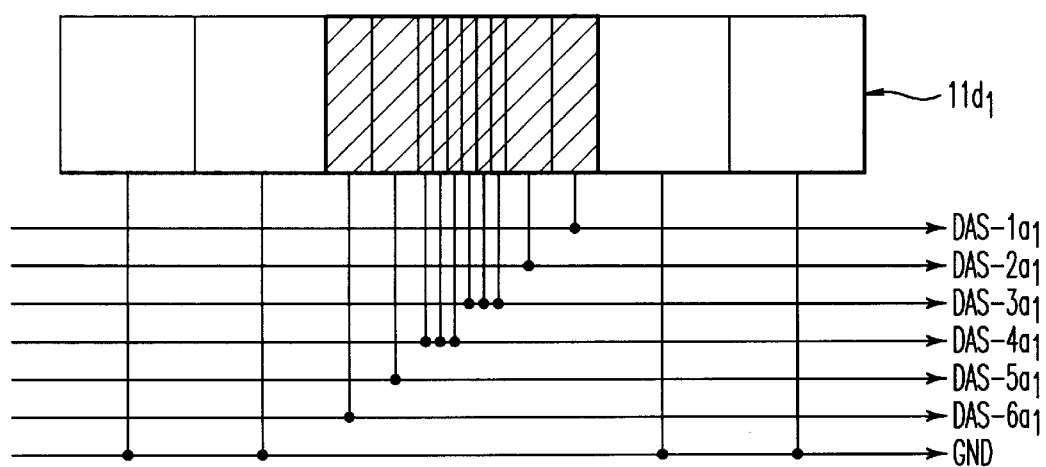
Figure 19:
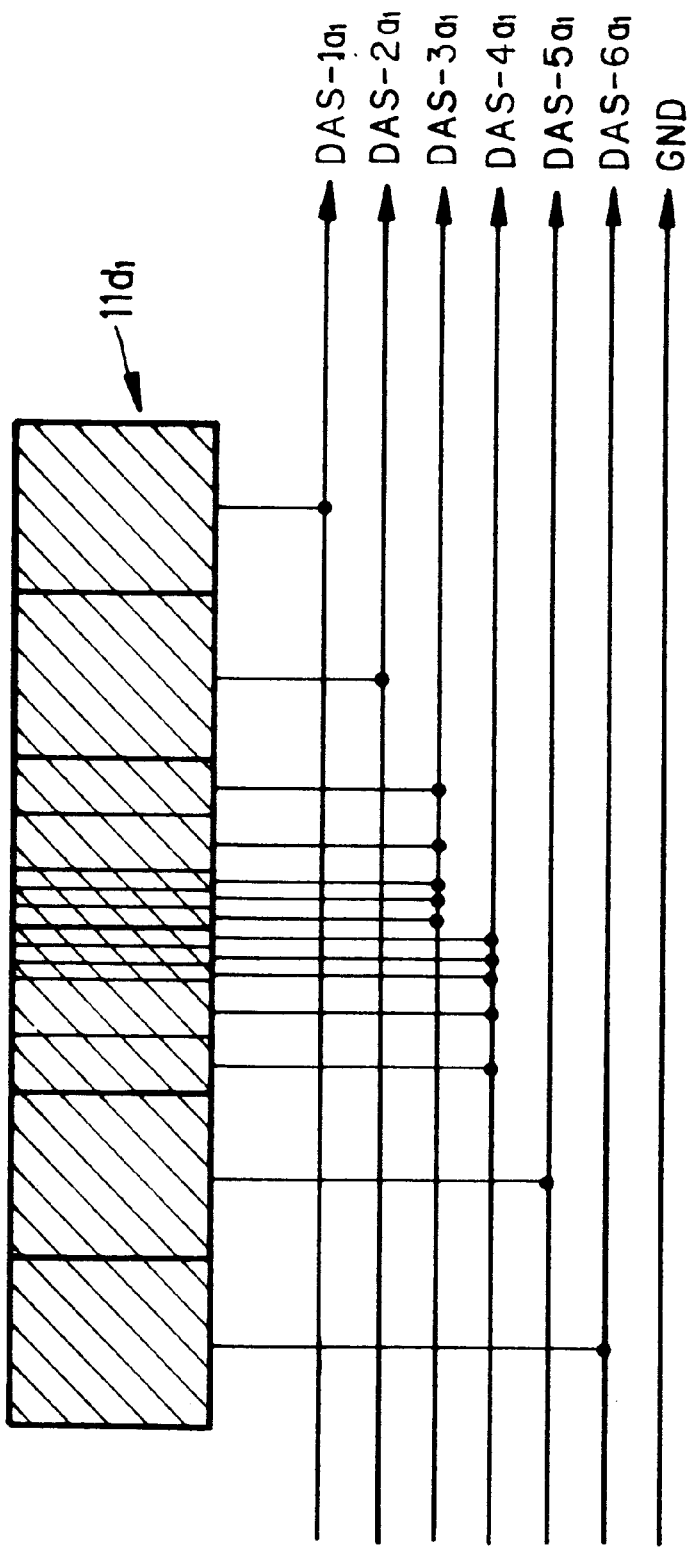
FIG. 19 shows the way of combining data items in a data acquisition mode in which data of 6 slices having the same pitch relative to adjoining slices is acquired with the pitch tripled, wherein data of 6 slices of 9 mm thick is acquired.

The ways of combining X-ray transmission data detected by the row of detecting elements 11d1 (for acquiring data of 6 slices having the same slice thickness) are shown in FIGS. 18A to 19.

Referring to FIG. 18A, the elements seg9a1 and seg9a2 and the elements seg3a1 and seg3a2 are grounded, the element seg1a1 is connected to the element DAS-1a1, the element seg1a2 is connected to the element DAS-2a1, the element seg1a3 is connected to the element DAS-3a1, the element seg1a4 is connected to the element DAS-4a1, the element seg1a5 is connected to the element DAS-5a1, the element seg1a6 is connected to the element DAS-6a1, and the elements seg3a3 and seg3a4 and the elements seg9a3 and seg9a4 are grounded. Thus, X-ray transmission data of 6 slices having a slice thickness of 1 mm can be sent to the elements DAS-1a1 to DAS-6a1.

Referring to FIG. 18B, the elements seg9a1 and seg9a2 are grounded, the element seg3a1 is connected to the element DAS-1a1, the element seg3a2 is connected to the element DAS-2a1, the elements seg1a1 to seg1a3 are connected to the element DAS-3a1, the elements seg1a4 to seg1a6 are connected to the element DAS-4a1, the element seg3a3 is connected to the element DAS-5a1, the element seg3a4 is connected to the element DAS-6a1, and the elements seg9a3 and seg9a4 are grounded. Thus, X-ray transmission data of 6 slices having a slice thickness of 3 mm can be sent to the elements DAS-1a1 to DAS-6a1.

Referring to FIG. 19, the element seg9a1 is connected to the element DAS-1a1, the element seg9a2 is connected to the element DAS-2a1, the elements seg3a1 and seg3a2 and the elements seg1a1 to seg1a3 are connected to the element DAS-3a1, the elements seg1a4 to seg1a6 and the elements seg3a3 and seg3a4 are connected to the element DAS-4a1, the element seg9a3 is connected to the element DAS-5a1, and the element seg9a4 is connected to the element DAS-6a1. Thus, X-ray transmission data of 6 slices having a slice thickness of 9 mm can be sent to the elements DAS-1a1 to DAS-6a1.

Figure 20A:
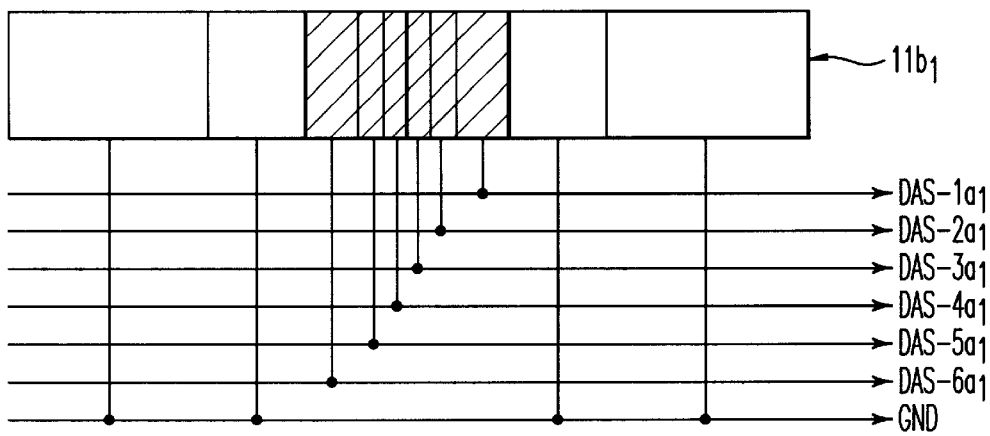
FIGS. 20A to 20C show as a variant (the segment structure for a DAS designed for handling 4 slices is adopted and a DAS designed for handling 6 slices is used in combination) the way of combining data items in a data acquisition mode in which data of 4 slices having different pitches relative to adjoining slices is acquired.
Figure 20B:
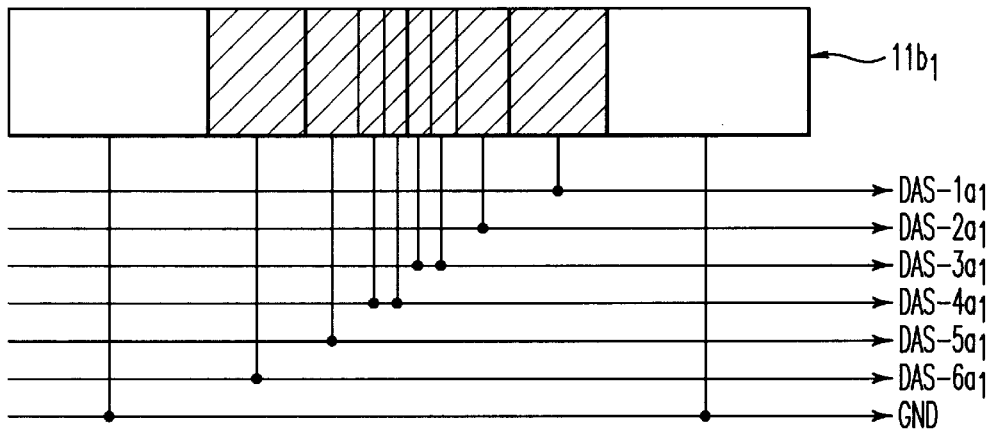
Figure 20C:
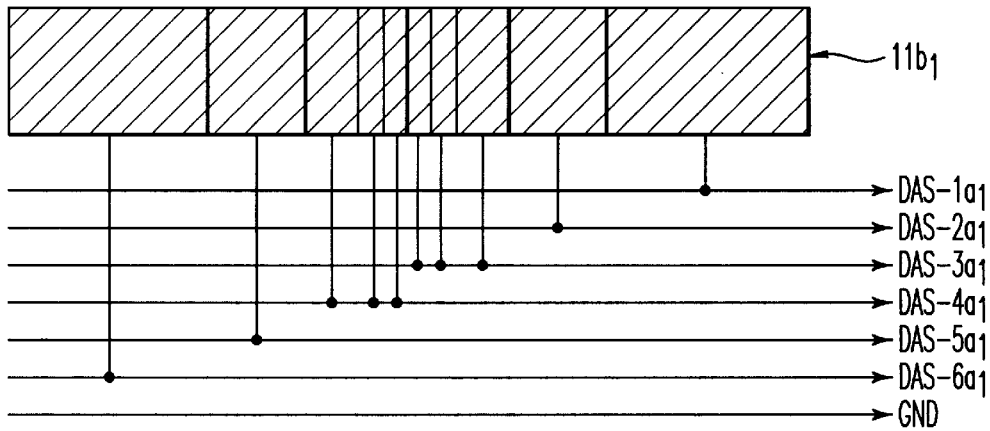

Even when structures conformable to any of the aforesaid rules on the relationship with the number of segments in the main detector are adapted to parts of the main detector and DAS, the same advantage can be exerted to the extent of the adaptation. FIGS. 20A to 20C show the ways of combining X-ray transmission data using the group of switches 20 in such a connection/data acquisition mode that for example, a row of detecting elements 11a1 constituting the first channel and having the segment structure shown in FIGS. 10 to 11B for acquiring data of 4 slices, and the DAS 21 (elements DAS-1a1 to DAS-6a1) designed for handling 6 slices are used in combination, and that data of 6 slices having different slice thicknesses (thick slices on both outer sides and thin slices in the center) are acquired.

Referring to FIG. 20A, like FIG. 11, the elements seg8a1 to seg4a1 are grounded, the element seg2a1 is connected the element DAS-1a1, the element seg1a1 is connected to the element DAS-2a1, the element seg1a2 is connected to the element DAS-3a1, the element seg1a3 is connected to the element DAS-4a1, the element seg1a4 is connected to the element DAS-5a1, the element seg2a2 is connected to the element DAS-6a1, and the elements seg4a2 and seg8a2 are grounded. Thus, X-ray transmission data of 6 slices having different slice thicknesses, that is, a slice of 2 mm thick, four slices of 1 mm thick, and a slice of 2 mm thick can be sent to the elements DAS-1a1 to DAS-6a1.

Referring to FIG. 20B, the element seg8a1 is grounded, the element seg4a1 is connected to the element DAS-1a1, the element seg2a1 is connected to the element DAS-2a1, the elements seg1a1 and seg1a2 are connected to the element DAS-3a1, the elements seg1a3 and seg1a4 are connected to the element DAS-4a1, the element seg2a2 is connected to the element DAS-5a1, the element seg4a2 is connected to the element DAS-6a1, and the element seg8a1 is grounded. Thus, X-ray transmission data of 6 slices having different slice thicknesses, that is, a slice of 4 mm thick, four slices of 2 mm thick, a slice of 4 mm thick can be sent to the elements DAS-1a1 to DAS-6a1.

Referring to FIG. 20C, the element seg8a1 is connected to the element DAS-1a1, the element seg4a1 is connected to the element DAS-2a1, the elements seg2a1 and the elements seg1a1 and seg1a2 are connected to the element DAS-3a1, the elements seg1a3 and seg1a4 and the element seg2a2 are connected to the element DAS-4a1, the element seg4a2 is connected to the element DAS-5a1, and the element seg8a2 is connected to the element DAS-6a1. Thus, X-ray transmission data of 6 slices having different slice thicknesses, that is, a slice of 8 mm thick, four slices of 4 mm thick, and a slice of 8 mm thick can be sent to the elements DAS-1a1 to DAS-6a1.

Referring to FIG. 20A to 20C, the thicknesses of 6 slices are 2 mm, 1 mm, 1 mm, 1 mm, 1 mm, and 2 mm in FIG. 20A, and 4 mm, 2 mm, 2 mm, 2 mm, 2 mm, and 4 mm in FIG. 20B. Thus, doubled thicknesses can be realized.

In the aforesaid embodiment, the group of switches 20 is structured so that the detecting elements belonging to each row of detecting elements can be connected to any elements of the DAS. If connection modes involving the detecting elements and the elements of the DAS are confined to presumable ones, a switch structure mode in which a reduced number of switches (switching devices) and a reduced number of control signals sent from the host controller 25 are employed can be adopted.

Figure 21:
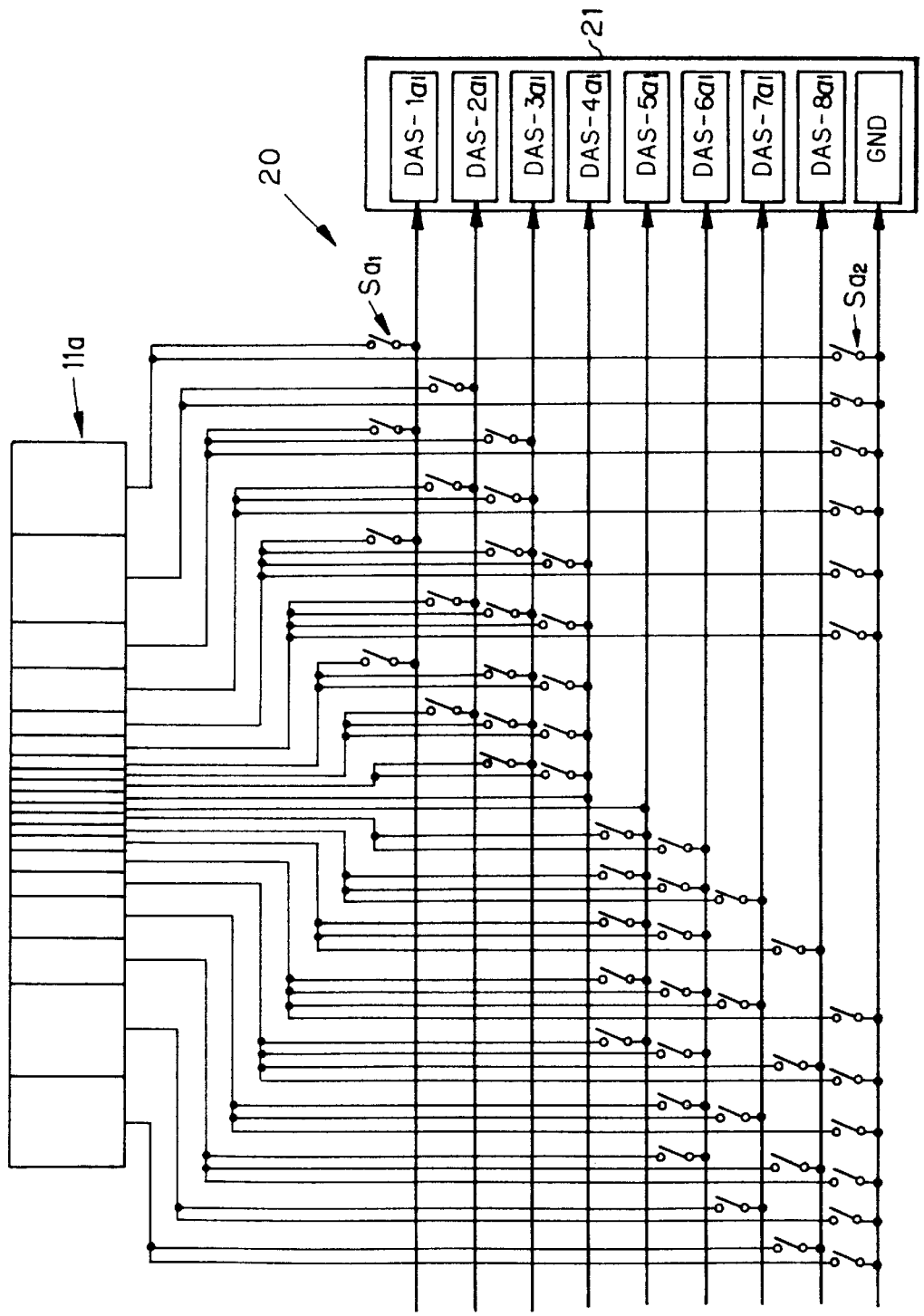
FIG. 21 shows a variant of the structure of switches permitting limited connection modes and including a minimum number of switches.

For example, when the rows of detecting elements covering 20 segments and constituting channels are connected to a DAS designed for handling 8 slices (See FIG. 5), if data of 8 slices having the same slice pitch relative to adjoining slices is acquired as shown in FIGS. 6A to 7B, the structure of a minimum number of switches enabling realization of the connection modes shown in FIGS. 6A to 7B is as shown in FIG. 21.

Specifically, in FIGS. 6A to 7B, for example, the element seg8a1 is connected merely to the element DAS-1a1 or ground. Two switches Sa1 and Sa2 should merely be included for controlling switching of connections to the element DAS-1a1 and ground.

FIG. 21 shows the structure including only the switches necessary for segments which is limited to such a connection mode that the segments are, as shown in FIGS. 6A to 7B, connected to a DAS designed for handling 8 slices having the same pitch relative to so adjoining ones. In the switch structure shown in FIG. 5, 9 switches (elements DAS-1a1 to DAS-8a1 and one ground GND) are needed for each of the segments (20 segments) belonging to rows of detecting elements constituting channels. A total of "9×20=180" switches are needed per channel. In the switch structure shown in FIG. 21, the number of switches is 52. The number of switches can thus be reduced greatly.

As mentioned above, assume that available data acquisition modes are limited to those in which projection data of 8 slices having the same slice pitch relative to adjoining ones is acquired (connection modes shown in FIGS. 6A to 7B). For realizing the connection modes shown in FIGS. 6A to 7B using a minimum number of control signals while reducing the number of the switches employed in the switch structure shown in FIG. 5, the connection modes shown in FIGS. 6A to 7B are regarded as four different connection modes, and each connection mode is regarded as one switching control pattern.

Taking for instance a pattern involving 8 slices of 1 mm thick in FIG. 6A, a total of six switches, that is, a switch S1G, switch S2G, switch S3G, switch S4G, switch S5G, and switch S6G are needed for grounding the elements seg8a1 and seg8a2, elements seg4a1 and seg4a2, and elements seg2a1 and seg2a2. A total of 8 switches, that is, a switch S71, switch S81, switch S91, switch S101, switch S111, switch S121, switch S131, and switch S141 are needed for connecting the elements seg1g1 to seg1a8 to the elements DAS-1a1 to DAS-8a1. A total of 6 switches, that is, a switch S15G, switch S16G, switch S17G, switch S18G, switch S19G, and switch S20G are needed for grounding the elements seg2a3 and seg2a4, elements seg4a3 and seg4a4, and elements seg8a3 and seg8a4. When switches are thus specified for each pattern, the number of switches needed per pattern is equal to the number of segments (20). A total of 20×4=80 switches are needed. The number of switches is much smaller than the number of switches (180) employed in the switch structure shown in FIG. 5 but larger than the aforesaid minimum number of switches. However, in this configuration, the number of control signals used to connect the host controller 25 to the group of switches 21 decreases. Taking the pattern shown in FIG. 6A for instance, all the switches for connecting the elements seg1a1 to seg1a8 to the elements DAS-1a1 to DAS-8a1 are turned on, the switches for grounding the elements seg8a1 and seg8a2, seg4a1 and seg42, and seg2a1 and seg2a2, and the switches for grounding the elements seg2a3 and seg2a4, seg4a3 and seg4a4, and seg8a3 and seg8a4 are all turned on. Only one control signal representing the on state should be sent over one signal line.

In this connection mode, therefore, the number of control signals is one per pattern. A total of 4 signal lines (minimum) are needed.

As far as the switch structure is limited to connection modes shown in FIGS. 6A to 7B in which the detecting elements are connected to a DAS designed for handling 8 slices having the same pitch relative to adjoining ones is concerned, either a structure including a minimum number of switches or a structure requiring a minimum number of control signals can be chosen. In either of the switch structures, the cost of parts including switches and the cost of installation can be minimized. Moreover, the switch structure shown in FIG. 5 has the merit of freedom in setting a connection mode (any of slice thicknesses of 1 mm, 2 mm, 4 mm, and 8 mm can be set freely). Which switch structure is chosen finally depends on which parameter emphasis should be placed (freedom, the number of switches, or the number of control signals). However, the aforesaid change in switch structure will not affect the major object and advantage of this embodiment, that is, "coexistence of high resolution and a wide scanned region."

Next, a switch structure including the beam trimmer 14 will be described as a variant of this embodiment. In the switch structure, a slice thickness of 5 mm, which has not been able to be selected in the past, can be selected by controlling connection or disconnection between the rows of detecting elements and a DAS through the on-off control of the group of switches 20 and by controlling the positions of the edges of a fan beam to be handled by the beam trimmer 14.

Figure 22A:
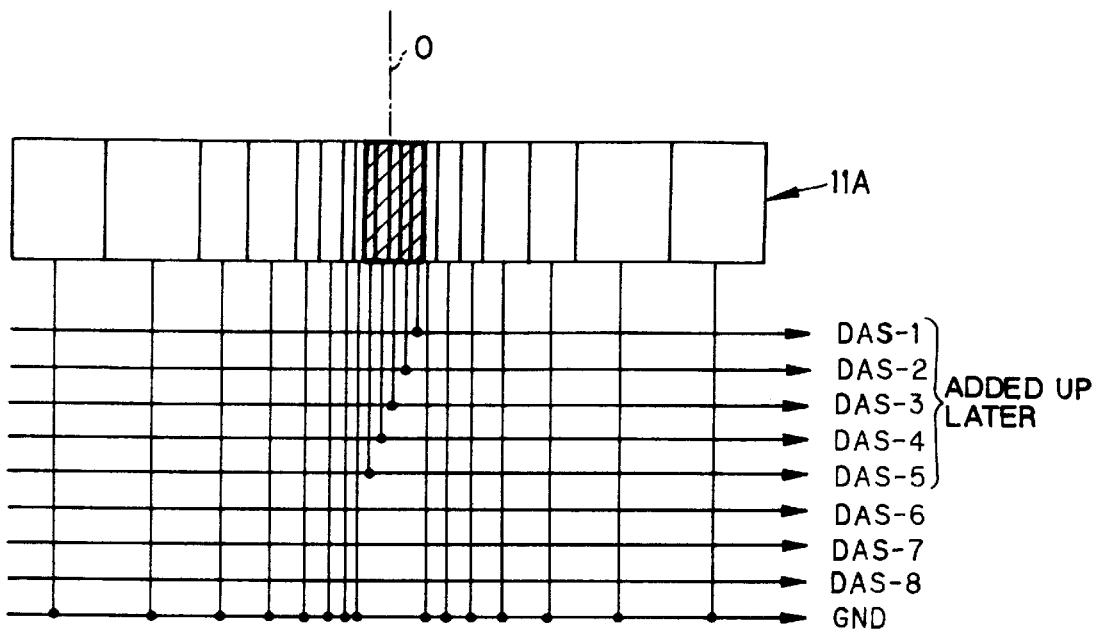
FIGS. 22A and 22B are diagrams showing a method of realizing a slice thickness unattainable by changing switches.

Taking for instance the switch structure in which X-ray transmission data detected by the row of detecting elements 11a1 constituting the first channel of the main detector 11 having a total of 20 segments, of which widths correspond to slice thicknesses of 1 mm to 8 mm, arranged is acquired using the DAS 21 (elements DAS-1a1 to DAS-8a1) designed for handling 8 slices (See FIG. 5), even when the setting of the group of switches 20 used for combination is changed, a slice of 5 mm thick could not have been defined symmetrically with respect to the center of the row covering the segments (between the elements seg1aand seg1a5)(See a dot-dash line (center line) O in FIG. 22A). A slice could, as shown in FIG. 22A, have been defined asymmetrically with respect to the center line O.

This variant makes it possible to detect X-ray transmission data of a plurality of slices having a slice thickness of 5 mm symmetrically with respect to the center line O.

To be more specific, according to the switch structure of this variant, the host controller 25 controls the on or off states of the switches S11 to S20G of the group of switches 20 under the conditions for scanning including the condition of a slice thickness (5 mm), and connects the element seg2a2 to the element DAS-1a1, the elements seg1a1 and seg1a2 to the element DAS-2a1, the element seg1a3 to the element DAS-3a1, the element seg1a4 to the element DAS-4a1, the element seg1a5 to the element DAS-5a1, the element seg1a3 to the element DAS-6a1, the elements seg1a7 and seg1a8 to the element DAS-7a1, and the element seg2a3 to the element DAS-8a1.

Figure 22B:
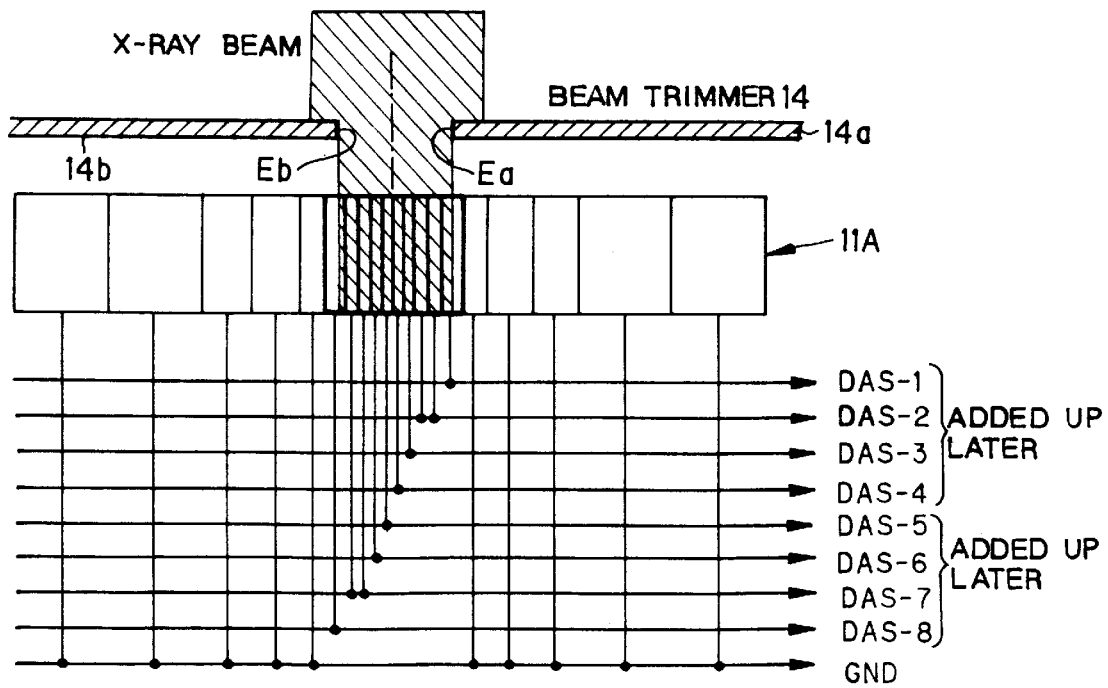

Next, the host controller 25 extends control to move the two X-ray shielding plates 14a and 14b of the beam trimmer 14 so that the edges Ea and Eb of the two X-ray shielding plates 14a and 14b can, as shown in FIG. 22B, align with the centers of the elements seg2a2 and seg2a3 respectively.

As a result, the elements seg2a2 and seg2a3 detect X-ray transmission data of a slice of 1 mm thick. Consequently, the elements DAS-1a1 to DAS-4a1 as a whole acquire projection data of a slice having a thickness of 5 mm. The projection data items acquired by the elements DAS-1a1 to DAS-4a1 are added up at a subsequent step (for example, a step of data processing carried out by the data processing unit 26), whereby projection data of the slice of 5 mm thick can be acquired. Likewise, the projection data items acquired by the elements DAS-5a1 to DAS-8a1 are added up at a subsequent step (for example, a step of data processing carried out by the data processing unit 26), whereby projection data of a slice having a thickness of 5 mm can be acquired.

In other words, according to this variant, when switching by the switches 20 is controlled to combine X-ray transmission data, the beam trimmer 14 is controlled at the same time. Consequently, a slice thickness (5 mm) that is not included in predetermined slice thicknesses (for example, 1 mm, 2 mm, 4 mm, and 8 mm) can be specified for data acquisition. This results in the greatly improved freedom in selecting a slice thickness.

The foregoing usage of the beam trimmer 14 is limited to a data acquisition mode in which data of slices of 1 mm thick or 2 mm thick is acquired. When a DAS permitting other data acquisition modes is included, a plurality of data items into which data of a slice of 5 mm thick is divided may be acquired and added up later. In this case, each acquired data item can be subjected to data processing such as interpolation. This contributes to minimization of artifacts deriving from the partial volume phenomenon.

For realizing the main detector 11 employed in the aforesaid embodiment and variant, the problem of dead spaces occupied by separators (reflector plates of, normally, about 0.1 mm thick) each interposed between segments becomes significant. That is to say, if the dead spaces become too large to be ignored, geometrical efficiency in a segment direction is absolutely lowered. Besides, since the segments become mutually different in size, the geometrical efficiency varies depending on the size of each segment.

Figure 23:
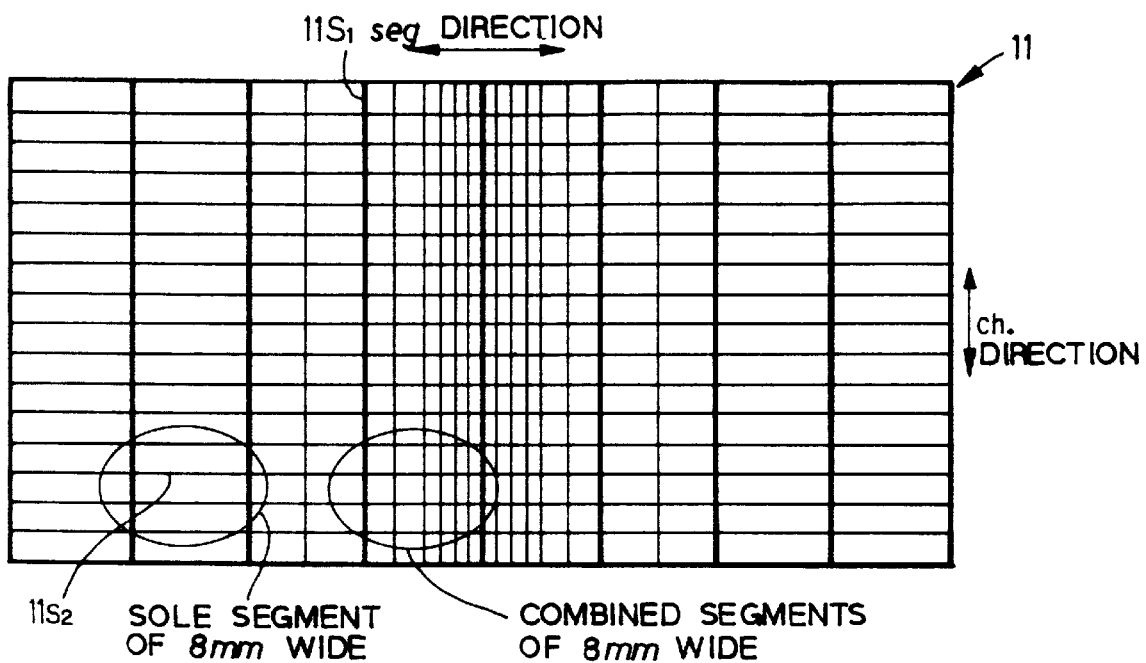
FIG. 23 shows the structure of a main detector (two-dimensional detector)

Assuming that, for example, the width of a dead space is 0.1 mm of a conventional level, as long as only a segment direction is considered with a channel direction ignored, geometrical efficiency differs between when data of a slice of 8 mm thick is, as shown in FIG. 23, acquired on the basis of data detected by a sole segment (FIGS. 23, 24Aa, and 24Ba) and when the data is acquired on the basis of data detected by a plurality of segments (FIGS. 23 and 23b).

Figure 24A:
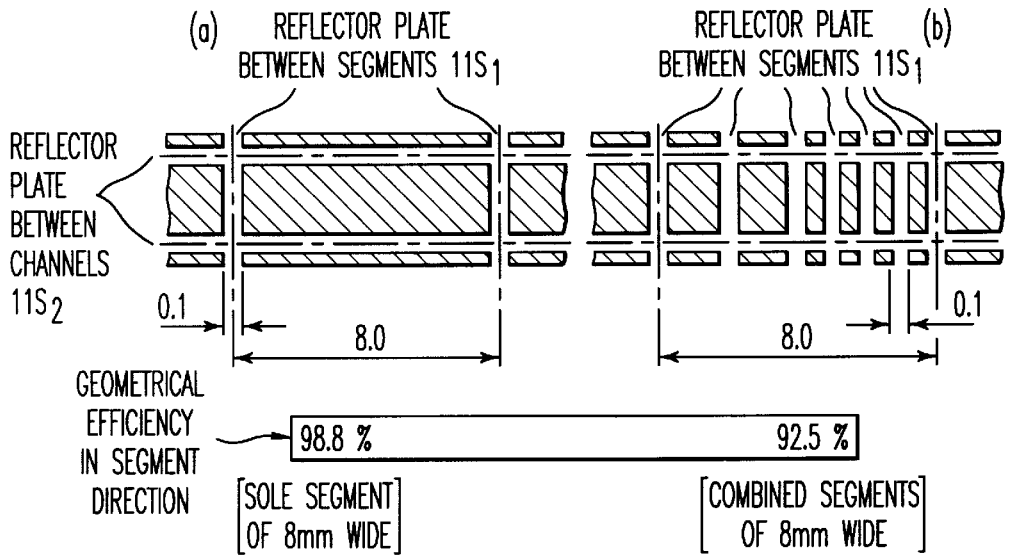
FIGS. 24A is a diagram showing the geometrical efficiency in a segment direction attainable when a reflector interposed between segments is thick.

Specifically, as shown in FIGS. 24Aa and 24Ab, the geometrical efficiency in a segment direction to the data detected by the sole segment of 8 mm wide (a) corresponding to a slice thickness of 8 mm is 98.8% or a quotient of (8−0.1)/8 because the segment is accompanied by only one dead space. By contrast, the geometrical efficiency in the segment direction to data detected by combining a plurality of segments whose widths realize a slice thickness of 8 mm is as low as 92.5% or a quotient of (8−0.6)/8 because six dead spaces are involved. This difference in geometrical efficiency leads to a difference in signal-to-noise ratio between acquired projection data items. Eventually, the signal-to-noise ratio of a reconstructed image becomes dependent on a position in the image and varies depending on an employed data item.

In another variant of this embodiment, a metallic thin film of, for example, about 0.01 mm thick made of, for example, aluminum foil, molybdenum, or tungsten is used as a separator (reflector plate) 11s1 to be interposed between segments in an effort to make a dead space smaller so as to minimize the difference in geometrical efficiency in a segment direction. This is attributable to the fact that a separator 11s2 to be interposed between channels cannot be made thinner than a certain thickness in order to avoid the shadow of a scattered radiation elimination collimator (slit) that is not shown, but that the minimum thickness of a separator to be interposed between segments is not limited to any value as long as the crosstalk of light rays propagating adjoining segments can be suppressed. For example, aluminum foil may be sandwiched between segments. An aluminum-deposited film or the like will do.

Figure 24B:
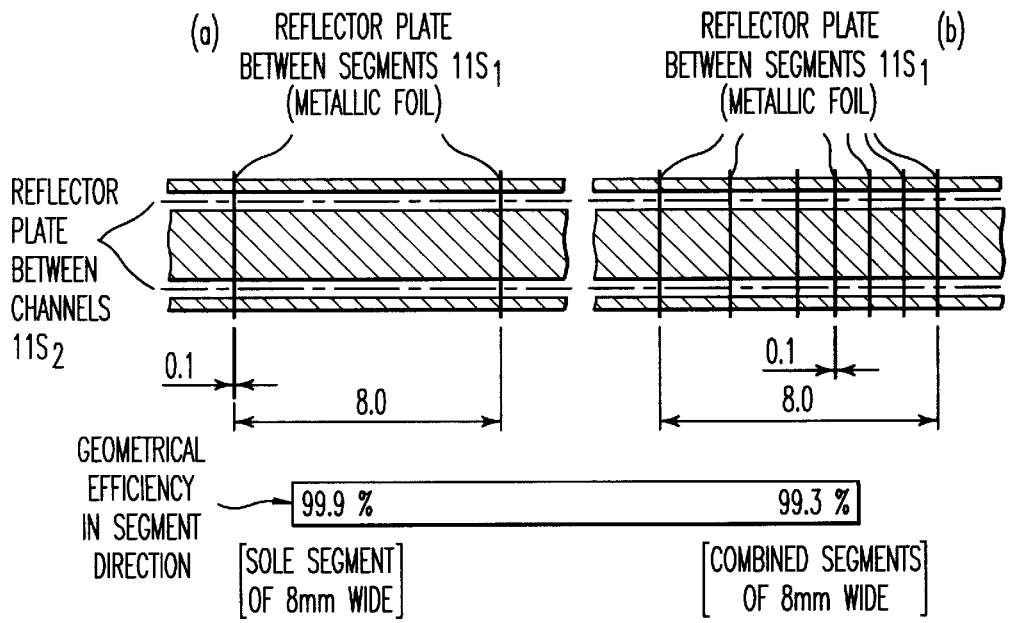
FIG. 24B is a diagram showing the geometrical efficiency in the segment direction attainable when the reflector interposed between segments is thin.

In this variant, for example, when foil of 10 micrometers thick is used as a separator, as shown in FIGS. 24Ba and 24Bb, the geometrical efficiency in a segment direction to data detected by a sole segment whose width corresponds to a slice thickness of 8 mm is 99.9%, and the geometrical efficiency in the segment direction to data detected by combined segments whose widths realize a slice thickness of 8 mm is 99.3%. The difference in geometrical efficiency is thus made smaller.

Next, an emergency procedure to be taken in case one element of the main detector 11 or DAS 21 in this embodiment fails will be described.

To begin with, X-ray transmission data acquired by one data acquisition element, or if a majority of detecting elements associated with one data acquisition element or an associated data acquisition element fails, data detected by the failing detecting elements or data acquired by the failing data acquisition element is replaced with data interpolated using data items (three or four data items) detected or acquired by surrounding elements (for example, if any detecting element of the main detector 11 fails, elements adjoining the failing element in segment directions or channel directions).

Figures 25A, 25B:
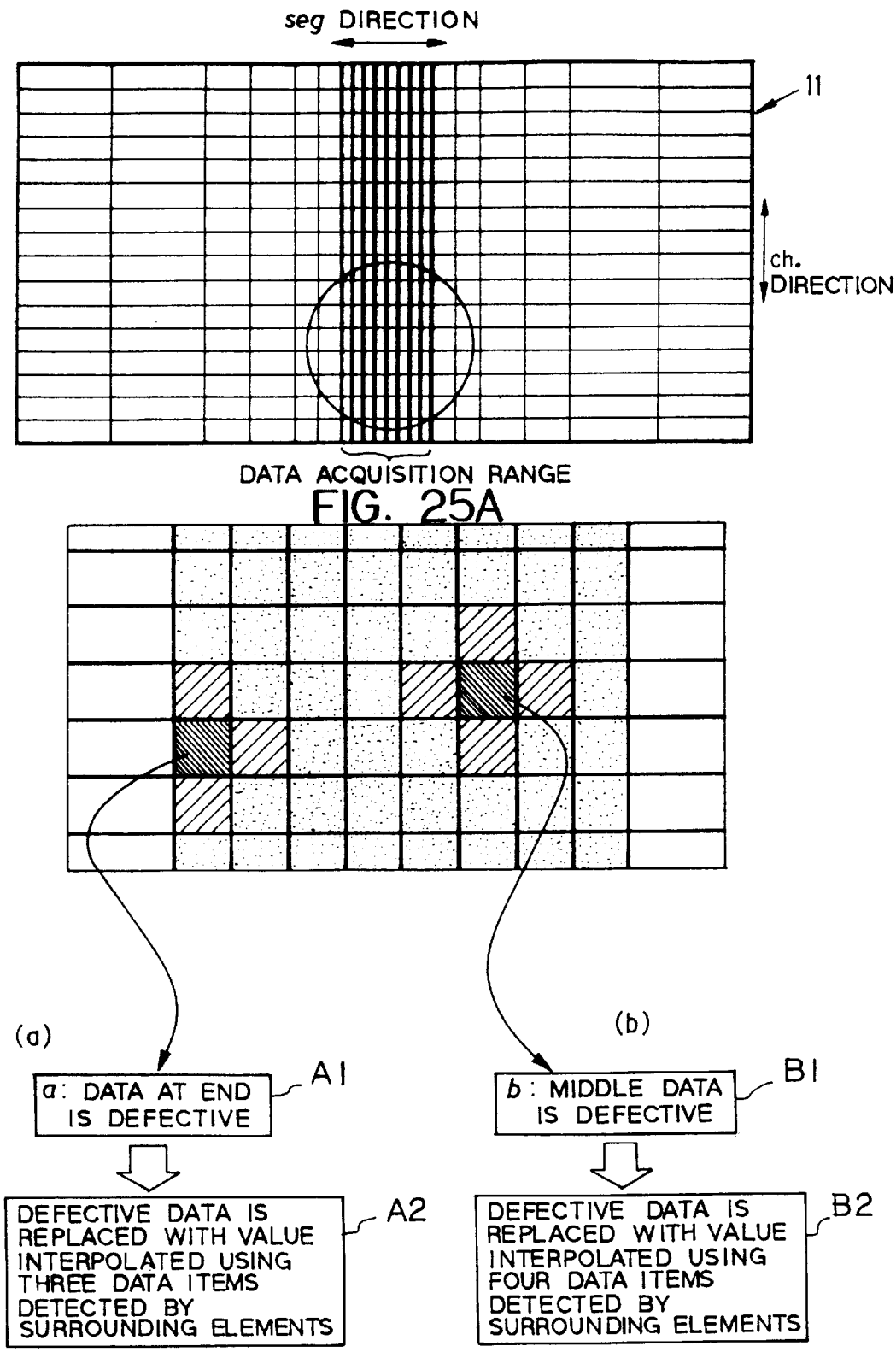
FIG. 25A is a diagram showing the structure of a main detector (two-dimensional detector)
FIG. 25B is an enlarged diagram of an encircled portion in FIG. 25A, wherein an emergency process to be adopted in case the whole of a detecting element concerned with one data becomes defective is shown in relation to the positions of failing segments.

The description will proceed by taking for instance the processing in which, as shown in FIG. 25A, data of slices having a pitch of 1 mm relative to adjoining ones is acquired using the reference segments of the detector having the segment structure shown in FIG. 5 (a range of data acquisition is defined by the elements seg1a1 to seg1a8).

If one of the segments defining the data acquisition range fails, since data detected by each segment corresponds to data of one slice, the whole of data of an associated slice becomes defective. Consequently, interpolation is carried out according to the position of the data detected by the failing element relative to the whole data.

If data detected by a failing element is located at an end in a slice (segment) direction of the whole acquisition data (data at an end is defective: described at step A1 in FIG. 25Ba), the data detected by the failing element is replaced with a value interpolated using three surrounding data items (one data item detected by an element adjoining the failing element in the segment direction and two data items detected by two adjoining elements lying in a channel direction (step A2).

If data detected by a failing element is, as shown in FIG. 25Bb, located in the middle in a slice (segment) direction of the whole acquisition data (middle data is defective: described at step B1 in FIG. 25Bb), the data detected by the failing element is replaced with a value interpolated using four data items (two data items detected by two elements adjoining the failing element in the segment direction and two data items detected by two elements adjoining it in a channel direction)(step B2).

If data detected by one failing segment is data to be combined with others, the precision of data produced by utilizing remaining data items is higher than the precision of data interpolated using surrounding data items while regarding the whole of combinative data as defective. In this case, therefore, a process to be executed on the basis of the idea that the sensitivity of a detector deteriorates by that of a failing segment is adopted.

Figure 26A:
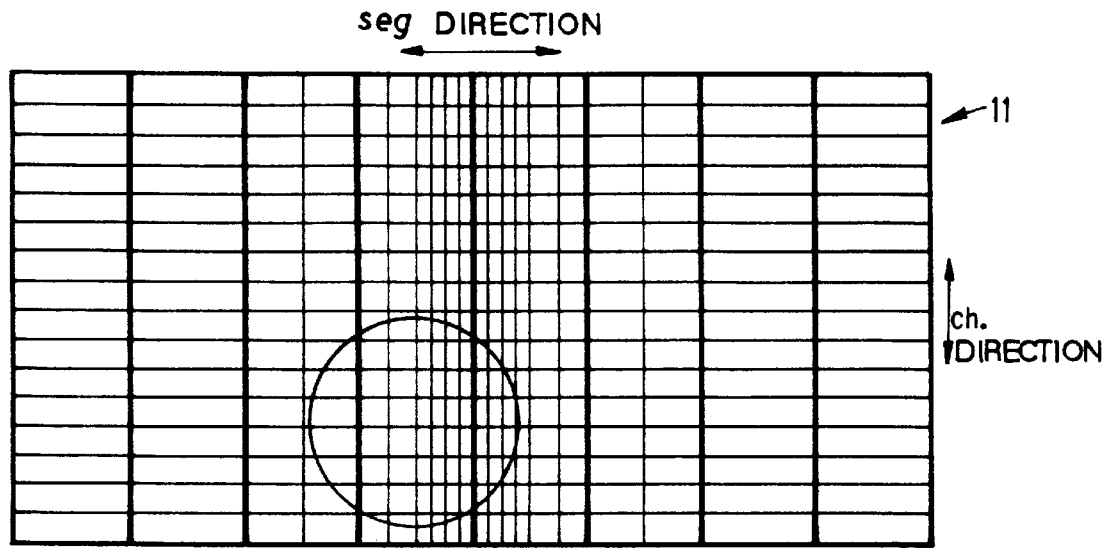
FIG. 26A is a diagram showing the structure of a main detector (two-dimensional detector)
Figure 26B:
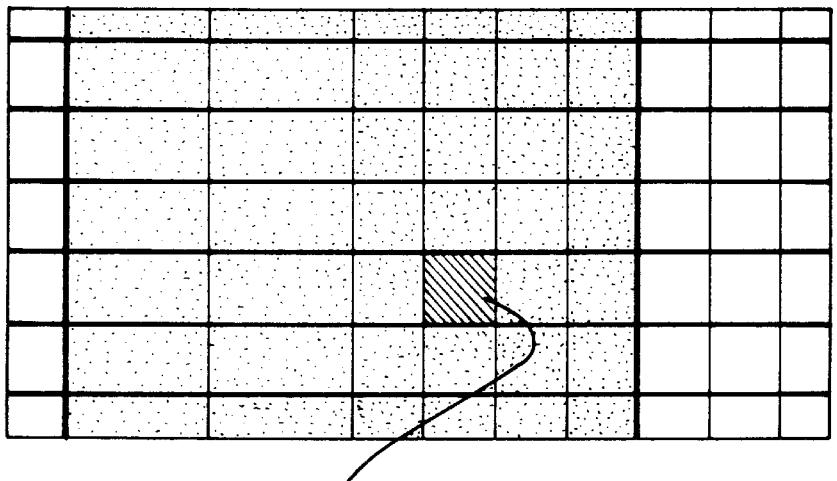
FIG. 26B is an enlarged diagram of an encircled portion of FIG. 26A, wherein an emergency process to be adopted in case part of detecting elements concerned with one data becomes defective is shown.
Figure 26B:
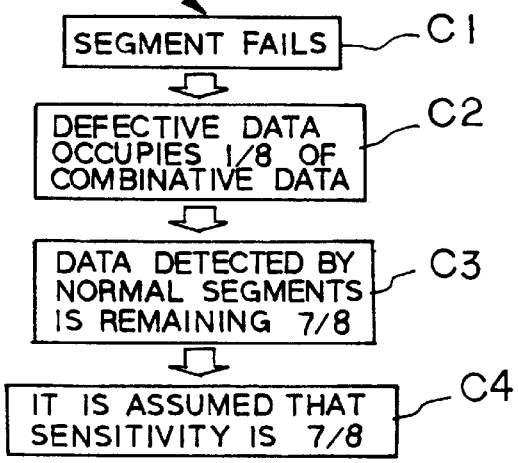

Assume that as shown in FIG. 26A, the detector having the segment structure shown in FIG. 5 is used to acquire data of 8 slices of 1 mm thick. In this case, if there is a failing segment among segments whose detected data items are to be combined and which are located in the center in a segment direction (step C1), data detected by the failing segment occupies one eighth of combinative data (step C2). In other words, one eighth of the whole data is defective, and data detected by surviving normal segments is the remaining seven eighths (step C3). Assuming that the sensitivity of the detecting elements (segments) providing data of a slice of 8 mm thick is regarded (read differently) as seven eighths (step C4). Sensitivity correction data (calibration data) of the main detector 11 is acquired again with consideration taken into that the sensitivity of the detecting elements to be combined to provide data of 8 slices is seven eighths. Thus, the influence of a failure can be eliminated to the greatest extent.

The point of the foregoing emergency procedure is to change processes according to a situation causing a failure (whether the detector or DAS fails, at which position a failing segment is located, etc.). The procedure for grasping the situation is also significant. Herein, a warm-up process to be executed at the time of system start-up or any other time will be discussed. In the warm-up process, a test scan is carried out several times for various purposes. For example, warm-up of the X-ray tube, check of the operation of the optical system unit, update of correction data (acquisition of air calibration data), and the like are carried out.

Grasping (checking) the situation in which the detection system fails can be carried out as part of the above process.

For example, when a detector comprising 20 segments and a DAS designed for handling 8 slices are used in combination, if data acquisition is repeated in four modes; a mode in which data of 8 slices of 1 mm thick is acquired, a mode in which data of 8 slices of 2 mm thick is acquired, a mode in which data of 8 slices of 4 mm thick is acquired, and a mode in which data of 8 slices of 8 mm thick is acquired, a failing segment of 1 mm wide, a failing segment of 2 mm wide, a failing segment of 4 mm wide, and a failing segment of 8 mm wide can be detected in the respective modes. A failure is judged from the criterion of whether or not the sensitivity of a segment concerned is deviated from an average value among segments having the same width by a certain threshold or more, or whether or not a change from test data obtained at the time of a warm-up performed in the previous day (or previous time) is deviated from an average value among segments having the same width by a certain threshold or more.

Figure 27:
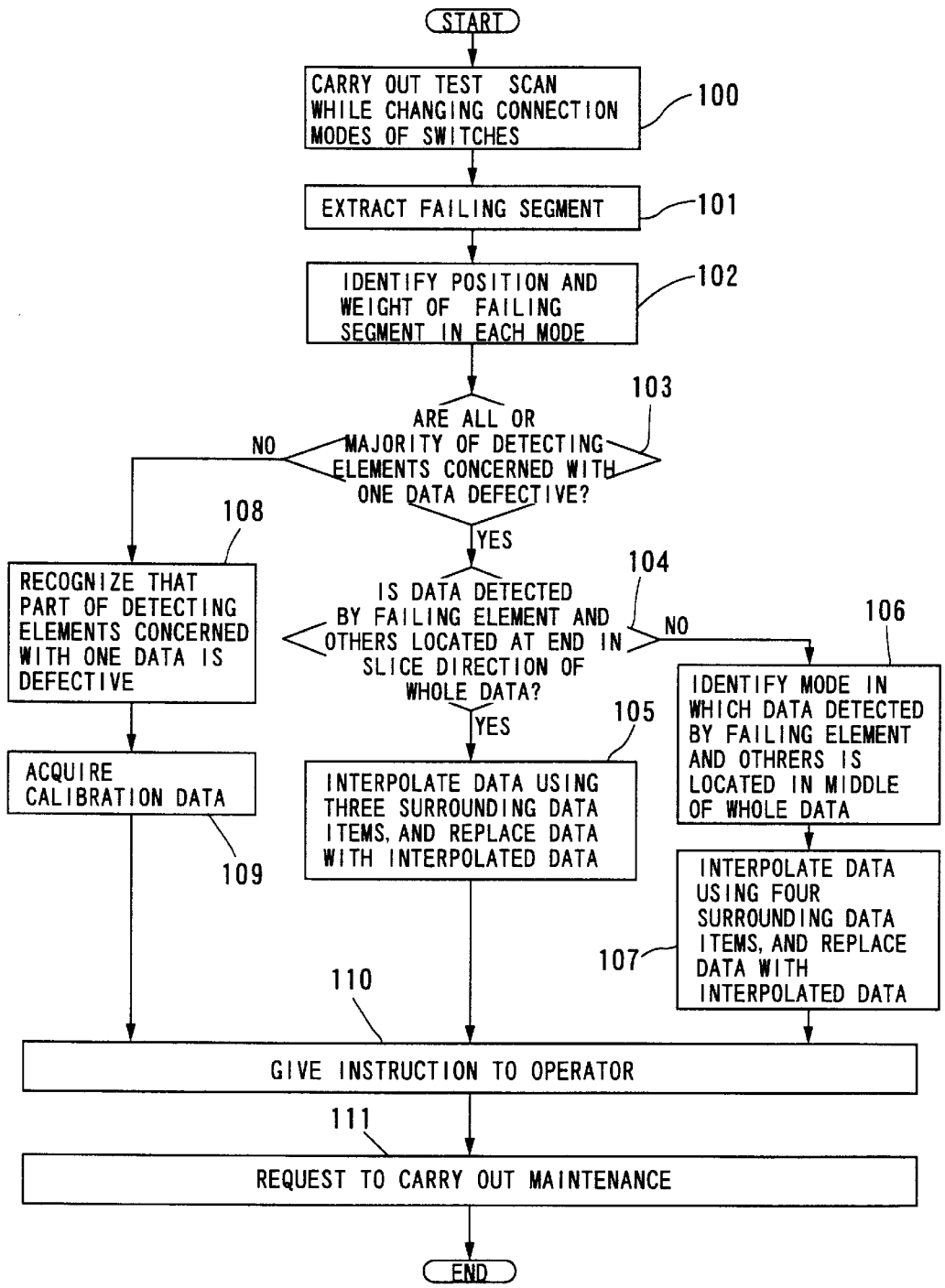
FIG. 27 is a simplified flowchart describing an example of processing to be performed by a host controller and other systems during the emergency processes shown in FIGS. 25 and 26.

An example of a series of operations is described in the flowchart of FIG. 27.

Referring to FIG. 27, during a warm-up, while changing connection modes of the switches of the group of switches 20, the host controller 25 controls drive of the high-voltage generating unit 15, gantry 3 (patient couch drive unit that is not shown, gantry drive unit 12, and the like), and the like under various conditions including the foregoing four modes, carries out a test scan, and acquires projection data repeatedly (step 100). Based on projection data acquired repeatedly in the same mode (in which data of slices having the same thickness is acquired), the host controller 25 then extracts a detecting element (segment), of which sensitivity is deviated from an average value among segments having the same width by a preset threshold or more, as a failing segment (step 101). The host controller 25 then identifies the position of a failing segment and the weight imposed on the failing segment in relation to each of the data acquisition modes (step 102). Based on the results of the identification, it is judged whether or not all (or a majority of) detecting elements concerned with data to be acquired by one data acquisition element (data detected by a sole segment or combinative data), or the associated data acquisition element has failed (step 103).

If the result of the judgment made at step 103 is in the affirmative (all or a majority of detecting elements concerned with one data are defective), the host controller 25 judges whether or not data detected by a failing element (segment) and others is located at an end in a slice direction of the whole data (step 104) and thus identifies a data acquisition mode. If the result of the judgment made at step 104 is in the affirmative, the host controller 25 interpolates data, as described at step A2 in FIG. 25B*a*, using data items detected by three adjoining segments surrounding the failing segment, replaces the data detected by the failing segment with the resultant interpolated data (step 105), and then passes control to step 110.

If the result of the judgment made at step 104 is in the negative, the host controller 25 identifies a data acquisition mode in which data detected by the failing segment and others is located in the middle of the whole data (step 106), interpolates data using data items detected by segments surrounding the failing segment as described at step B2 in FIG. 25B*b*, replaces the data detected by the failing segment with the interpolated data (step 107), and then passes control to step 110.

If the result of the judgment made at step 103 is in the negative, the host controller 25 recognizes that part of detecting elements concerned with one data is defective (step 108), acquires sensitivity correction data (water calibration data) for this mode (step 109), and passes control to step 110. When a phantom or the like need to be placed to acquire correction data, a request for acquisition of correction data (water calibration data) may be issued via the display unit 29, or control may automatically be passed to a correction data acquisition mode.

The contents of the processing of steps 100 to 109 are not the same relative to one failing segment but different among all connection modes in which the segment is employed. Even when a failing segment is the same, the contents of the processing differ among data acquisition modes. That is to say, in a certain data acquisition mode (in which data detected by the segment alone is acquired as data of one slice), data is interpolated using surrounding data items, and data detected by the failing segment is replaced with the interpolated data. In another data acquisition mode (in which segments are combined to provide data of a certain slice), calibration data is acquired. These processes are automatically carried out in the warm-up process.

At step 110, the host controller 25 prompts the operator O to carry out maintenance (step 111) by outputting and displaying occurrence of a failing segment via, for example, the display unit 29, and thus completes an emergency procedure.

As mentioned above, according to this embodiment, even if one element (segment) of, for example, the main detector fails, the position of the failing segment is automatically identified, and the precision of data can be optimized according to the position. Consequently, an optimal emergency procedure (for example, data interpolation or sensitivity correction) can be carried out. According to this embodiment, the ability to cope with an emergency in which a detecting element of the main detector or an element of a DAS fails is improved greatly compared with that in the prior art. Eventually, high diagnostic precision can be retained.

The aforesaid flowchart describes an emergency procedure to be adopted in case one detecting element (segment) of the main detector 11 fails. Even if one element of the DAS 21 fails, a procedure substantially identical to the one described in FIG. 27 would be carried out. Consequently, the same advantage as the one described previously can be exerted. In this case, fundamentally, the whole of data acquired by the data acquisition element becomes defective. Data is therefore interpolated using data items acquired by elements surrounding the failing element, and the data acquired by the failing element is replaced with the interpolated data.

As described so far, according to the X-ray CT scanner, the X-ray detecting elements having irregular pitches in a slice-thickness direction of the two-dimensional detector relative to adjoining elements, and the plurality of data acquisition elements arranged in the slice-thickness direction and a channel direction and associated with X-ray detecting elements can be selectively connected according to the condition of a slice thickness by controlling the on or off states of the group of switches composed of a plurality of switches. By modifying the structure of the detecting elements having an irregular pitch relative to adjoining elements or changing connection modes, both high resolution (fine slice pitch) a slice-thickness direction (body-axis direction) and a wide scanned region therein can be realized. Consequently, the diagnostic performance of the X-ray CT scanner (multi-slice X-ray CT scanner) having the two-dimensional detector can be improved, and the practicality thereof can be improved.

Furthermore, when the detecting elements are connected to the data acquisition elements with at least part of the detecting elements combined by specifying a control pattern for controlling the on or off states of the switches according to the condition of a slice thickness, data of slices having various slice thicknesses can be acquired. That is to say, the freedom in selecting the slice thickness of a slice whose data is acquired can be expanded, and the diagnostic precision and efficiency of an X-ray CT scanner can be improved.

Still furthermore, an optimal failure correction process can be selected according to the position of an X-ray detecting element or the like (for example, a position in a slice direction) in order to correct data detected by a failing element. If any detecting element should fail, an optimal emergency procedure can be carried out without fail. Eventually, the reliability of an X-ray CT scanner having a two-dimensional detector composed of a plurality of X-ray detecting elements can be improved.

The present invention is not limited to the lists and/or contents which have been described above, and may be modified into various ways without departing from the gist of the invention.

What is claimed is:

1. An X-ray CT scanner in which an X-ray beam is radiated and scanned in a predetermined slice-thickness direction, a direction orthogonal to the slice-thickness direction being defined as a channel direction, an object being placed in a position to be radiated by the X-ray beam, the scanner comprising:

a two-dimensional X-ray detector having a plurality of X-ray detecting elements arranged in a two-dimensional array constituting both rows arranged along the slice-thickness direction and columns arranged along the channel direction, each X-ray detecting element providing a detected signal, X-ray detecting elements constituting each row of the two-dimensional array being formed on unequal element pitches;

a data acquisition system having a plurality of data acquiring elements arranged in a two-dimensional array of rows corresponding to the slice-thickness direction and columns corresponding to the channel direction, configured to acquire signals detected by the two-dimensional X-ray detector and to produce digital data based on the detected signals, each row of the two-dimensional array of data acquiring elements has fewer number of elements than each row of the two-dimensional array of X-ray detecting elements;

switching means comprising a group of switches electrically intervening between the X-ray detector and the data acquiring system, each switch being on/off switchable, said group of switches electrically independently connecting each of the X-ray detecting elements of each row of detecting elements to all the data acquiring elements of a respective row of data acquiring elements;

means for electrically combining the detected signals provided by X-ray detecting elements residing in at least two columns designated in the array of the X-ray detecting elements row by row into a signal corresponding to multiple slices and for providing the combined signal to a particular data acquiring element of the respective row in the array of the data acquiring elements by controlling the switch means in accordance with a designated slice-thickness condition relating to the multiple slices; and means for producing multiple slice images from the digital data provided by the data acquisition system in response to the slice-thickness condition.

2. The scanner of claim 1, further comprising means for inputting the slice-thickness condition based on operator's instructions.

3. The scanner of claim 1, wherein each row of X-ray detecting elements is composed of first and second groups of X-ray detecting elements, the first group of X-ray detecting elements with each detecting element having a specified minimum element pitch and being positioned in the center of the row, and the second group of X-ray detecting elements with each detecting element having a greater element pitch than the minimum element pitch being positioned next to the first group in the row.

4. The scanner of claim 3, wherein the combining means comprises;

means for electrically controlling an on/off state of each of the switches in reply to the designated slice-thickness condition.

5. The scanner of claim 4, wherein the means for controlling an on/off state of each switch comprises a device which controls the on/off state of each of the switches so that each row of data acquiring elements produces a plurality of tomographic image data for the multiple slice images, each slice having a same one specified slice thickness.

6. The scanner of claim 4, wherein the means for controlling the on/off state of each switch comprises a device which controls the on/off state of each of the switches so that at least three of the X-ray detecting elements of any row including the detecting elements of the first group are electrically connected to at least two of the data acquiring elements of a respective row of data acquiring elements, when the designated slice-thickness condition includes a slice-thickness value greater than the specified minimum element pitch.

7. The scanner of claim 1, wherein the unequal element pitches within each row of the X-ray detecting elements is selected such that a slice thickness for the multiple slice images doubles for each successive combination of the X-ray detecting elements implemented by the switching means and the combining means according to the designated slice thickness condition.

8. The scanner of claim 1, wherein the unequal element pitches within each row of the X-ray detecting elements is selected such that a slice thickness for the multiple slice images triples for each successive combination of the X-ray detecting elements performed by the switching means and the combining means according to the designated slice thickness condition.

9. The scanner of claim 4, wherein the controlling means includes an element controlling the on/off status of each of the switches so that the data produced by the data acquiring elements provide the multiple slices of which slices thicknesses are composed of at least two thicknesses.

10. The scanner of claim 6, wherein the controlling means control the switches so as to selectively connect only desired ones of the X-ray detecting elements of each row of X-ray detecting elements on the basis of a desired on/off switch control pattern to the data acquiring elements a respective row of data acquiring elements.

11. The scanner of claim 4, further comprising:

a beam trimmer having two X-ray shielding plates movable along the slice-thickness direction and arranged on an X-ray incidence surface side of the two-dimensional X-ray detector, and, means for controlling an edge position of each of the X-ray shielding plates in the slice-thickness direction in accordance with the designated slice-thickness condition, wherein both the on/off control of each of the switches by the control means, and the edge position control of each of the X-ray shielding plates permit data acquisition for desired slice pitches of the multiple slice images.

12. The scanner of claim 1, further comprising means for detecting a failing element which has failed in either detection or acquisition, residing in either the array of X-ray detecting elements or the array of data acquiring elements, means for determining a two-dimensional position of the failing element on each array, and means for correcting the data from the failing element on the basis of the two-dimensional position determined by the determining means.

13. The scanner of claim 12, wherein the failing element is an X-ray detecting element, and the data correcting means comprises first means for determining if a first condition of the data detected from the failing element occupying at least a specified amount of the data acquired by the data acquiring elements is accomplished or not, second means for determining if a second condition of the data detected by the failing element is positioned in the slice-thickness direction at edges of a group of data acquired by the entire data acquiring elements is accomplished or not when the first condition has been accomplished, first means for interpolating the data detected from the failing element with detected data from three elements surrounding the failing element when the second condition has been accomplished, and second means for interpolating the data detected from the failing element with detected data from four elements surrounding the failing element when the second condition has not been accomplished.

14. The scanner of claim 13, wherein the data correcting means further comprise means for correcting sensitivity data for the entire X-ray detecting elements provided the first condition has not been accomplished.

15. The scanner of claim 1, wherein the plurality of X-ray detecting elements two-dimensionally arranged in the two-dimensional X-ray detector are separated by separators, the separators including a sub separator placed along the slice-thickness direction, and the separators are made of a thin film of metal.

16. The scanner of claim 3, wherein the first group of detecting elements consists of a plurality of detecting elements each having the specified minimum element pitch and the second group of detecting elements consists of a plurality of subgroups of detecting elements different in element pitches subgroup by subgroup, each subgroup of detecting elements further consisting of a plurality of detecting elements having a specific element pitch.

17. The scanner of claim 18, wherein all the detecting elements of the second group are aligned along each row in the order of largeness of the element pitches from a position adjacent to the first group to each end.

* * * * *